US009711064B2

(12) United States Patent
Nielson et al.

(10) Patent No.: US 9,711,064 B2
(45) Date of Patent: Jul. 18, 2017

(54) SYSTEMS AND METHODS FOR CALCULATING TEXT DIFFICULTY

(71) Applicant: Voxy, Inc., New York, NY (US)

(72) Inventors: Katharine Nielson, Richmond, VA (US); Kasey Kirkham, New York, NY (US); Na'im Tyson, Mount Vernon, NY (US); Andrew Breen, New York, NY (US)

(73) Assignee: VOXY, Inc., New York, NY (US)

( * ) Notice: Subject to any disclaimer, the term of this patent is extended or adjusted under 35 U.S.C. 154(b) by 191 days.

(21) Appl. No.: 14/180,943

(22) Filed: Feb. 14, 2014

(65) Prior Publication Data

US 2014/0295384 A1    Oct. 2, 2014

Related U.S. Application Data

(60) Provisional application No. 61/765,105, filed on Feb. 15, 2013.

(51) Int. Cl.
*G09B 19/04* (2006.01)
*G09B 19/06* (2006.01)
(Continued)

(52) U.S. Cl.
CPC .............. *G09B 19/06* (2013.01); *A61B 5/048* (2013.01); *A61B 5/162* (2013.01); *A61B 5/165* (2013.01);
(Continued)

(58) Field of Classification Search
CPC ... G09B 5/00; G09B 5/02; G09B 5/06; G09B 7/00; G09B 7/02; G09B 7/06; G09B 7/08;
(Continued)

(56) References Cited

U.S. PATENT DOCUMENTS 5,820,386 A * 10/1998 Sheppard, II .......... G09B 5/065
434/169
5,995,921 A    11/1999 Richards et al.
(Continued)

OTHER PUBLICATIONS

International Search Report and Written Opinion dated Aug. 18, 2014 corresponding to International Patent Application No. PCT/US2014/016354, 20 pages.
(Continued)

*Primary Examiner* — Nikolai A Gishnock
(74) *Attorney, Agent, or Firm* — Eric L. Sophir; Dentons US LLP

(57) ABSTRACT

Disclosed are systems, methods, and products for language learning that automatically extracts keywords from resources using various natural-language processing product features, which can be combined with custom-designed learning activities to offer a needs-based, adaptive learning methodology. The system may receive resources having text and then determine a text difficulty score that predicts how difficult the resource is for language learners based on any number of factors, including any number of semantic and syntactic features of the text. Training resources labeled with metadata may be used to train a statistical model for determining difficulty scores of newly received text. Resources may be grouped based on difficulty score, and groups of resources may correspond to language learners' proficiency levels.

13 Claims, 10 Drawing Sheets

(51) Int. Cl.

| | | |
|---|---|---|
| *G09B 19/08* | (2006.01) | |
| *G09B 5/04* | (2006.01) | |
| *G09B 5/06* | (2006.01) | |
| *G09B 7/00* | (2006.01) | |
| *G09B 7/04* | (2006.01) | |
| *G09B 17/00* | (2006.01) | |
| *A61B 5/16* | (2006.01) | |
| *A61B 5/048* | (2006.01) | |
| *G09B 5/02* | (2006.01) | |
| *G06F 17/27* | (2006.01) | |
| *G09B 5/00* | (2006.01) | |
| *G09B 7/08* | (2006.01) | |
| *A61B 5/00* | (2006.01) | |
| *A61B 5/11* | (2006.01) | |
| *A61B 5/0484* | (2006.01) | |
| *A61B 5/0476* | (2006.01) | |

(52) U.S. Cl.
 CPC ............. *A61B 5/411* (2013.01); *A61B 5/486* (2013.01); *G06F 17/274* (2013.01); *G06F 17/2705* (2013.01); *G06F 17/275* (2013.01); *G09B 5/00* (2013.01); *G09B 5/02* (2013.01); *G09B 7/08* (2013.01); *A61B 5/0002* (2013.01); *A61B 5/0476* (2013.01); *A61B 5/04842* (2013.01); *A61B 5/1124* (2013.01); *A61B 5/4064* (2013.01); *A61B 5/4076* (2013.01); *A61B 5/4088* (2013.01); *A61B 5/4842* (2013.01)

(58) Field of Classification Search
 CPC ........ G09B 19/00; G09B 19/04; G09B 19/06; A61B 5/411; A61B 5/40082; A61B 5/4088; A61B 5/4064; A61B 5/162; A61B 5/4842; A61B 5/4076; A61B 5/1124; A61B 5/0002; A61B 5/165; A61B 5/486; A61B 5/0476; A61B 5/048; A61B 5/04842
 USPC ................................ 434/156, 157, 159, 167
 See application file for complete search history.

(56) References Cited

U.S. PATENT DOCUMENTS

| | | | |
|---|---|---|---|
| 6,341,960 B1 * | 1/2002 | Frasson | G09B 7/02 434/118 |
| 7,062,441 B1 * | 6/2006 | Townshend | G09B 19/04 434/353 |
| 8,202,097 B1 | 6/2012 | Brittingham et al. | |
| 8,602,789 B2 * | 12/2013 | Hallowell | G09B 7/00 434/167 |
| 9,047,785 B2 | 6/2015 | Chaniotakis et al. | |
| 9,262,935 B2 | 2/2016 | Nielson et al. | |
| 9,324,242 B2 | 4/2016 | Chaniotakis et al. | |
| 2004/0018479 A1 | 1/2004 | Pritchard et al. | |
| 2004/0234936 A1 | 11/2004 | Ullman et al. | |
| 2005/0080613 A1 | 4/2005 | Colledge et al. | |
| 2005/0233288 A1 * | 10/2005 | McGrath | G09B 7/00 434/118 |
| 2005/0273017 A1 * | 12/2005 | Gordon | A61B 5/048 600/544 |
| 2006/0024654 A1 * | 2/2006 | Goodkovsky | G09B 7/02 434/350 |
| 2006/0154226 A1 * | 7/2006 | Maxfield | G09B 7/00 434/323 |
| 2007/0172809 A1 * | 7/2007 | Gupta | G09B 7/00 434/350 |
| 2007/0206017 A1 | 9/2007 | Johnson et al. | |
| 2008/0166693 A1 * | 7/2008 | Gifford | G09B 7/00 434/322 |
| 2008/0254434 A1 * | 10/2008 | Calvert | G09B 5/00 434/350 |
| 2009/0174142 A1 * | 7/2009 | Sullivan | A63F 3/0423 273/272 |
| 2009/0306534 A1 * | 12/2009 | Pizzagalli | A61B 5/0476 600/544 |
| 2010/0273138 A1 | 10/2010 | Edmonds et al. | |
| 2011/0065069 A1 * | 3/2011 | Duffy | G09B 19/00 434/156 |
| 2011/0065070 A1 * | 3/2011 | Duffy | G09B 7/00 434/159 |
| 2011/0065071 A1 * | 3/2011 | Duffy | G09B 7/00 434/167 |
| 2011/0065072 A1 * | 3/2011 | Duffy | G09B 7/00 434/167 |
| 2011/0065073 A1 * | 3/2011 | Duffy | G09B 7/00 434/167 |
| 2011/0065082 A1 * | 3/2011 | Gal | G09B 7/02 434/365 |
| 2011/0111377 A1 | 5/2011 | Dekkers | |
| 2011/0191098 A1 | 8/2011 | Thomas et al. | |
| 2012/0077160 A1 * | 3/2012 | DeGutis | G09B 7/02 434/236 |
| 2012/0115112 A1 * | 5/2012 | Purushotma | G09B 19/06 434/157 |
| 2012/0158527 A1 | 6/2012 | Cannelongo et al. | |
| 2012/0244510 A1 | 9/2012 | Watkins, Jr. | |
| 2012/0322035 A1 | 12/2012 | Julia et al. | |
| 2012/0329027 A1 * | 12/2012 | Lewolt | G06Q 10/101 434/322 |
| 2013/0004930 A1 * | 1/2013 | Sorenson | G09B 7/02 434/350 |
| 2013/0216985 A1 * | 8/2013 | de Villers-Sidani | A61B 5/04842 434/236 |
| 2013/0323692 A1 * | 12/2013 | Freimuth | G09B 5/00 434/169 |
| 2014/0024009 A1 * | 1/2014 | Nealon | G09B 5/12 434/362 |
| 2014/0272847 A1 * | 9/2014 | Grimes | G09B 19/00 434/236 |
| 2014/0272914 A1 * | 9/2014 | Baraniuk | G06N 99/005 434/362 |
| 2014/0279727 A1 * | 9/2014 | Baraniuk | G06N 99/005 706/11 |
| 2014/0295384 A1 | 10/2014 | Nielson et al. | |
| 2014/0297266 A1 | 10/2014 | Nielson et al. | |
| 2014/0308645 A1 | 10/2014 | Chaniotakis et al. | |
| 2014/0335497 A1 * | 11/2014 | Gal | G09B 7/00 434/323 |
| 2014/0342320 A1 | 11/2014 | Nielson et al. | |
| 2014/0342323 A1 | 11/2014 | Nielson et al. | |
| 2014/0370479 A1 * | 12/2014 | Gazzaley | A61B 5/162 434/322 |
| 2014/0370487 A1 | 12/2014 | Chaniotakis et al. | |
| 2015/0057994 A1 * | 2/2015 | Fang | G09B 5/125 704/4 |
| 2015/0242979 A1 * | 8/2015 | Abts | G09B 5/00 705/328 |
| 2015/0294577 A1 * | 10/2015 | Kullok | A61B 5/743 434/236 |
| 2015/0325133 A1 | 11/2015 | Gaglani et al. | |
| 2016/0012746 A1 * | 1/2016 | Haran | G06F 17/2795 434/169 |
| 2016/0035237 A1 * | 2/2016 | Nealon | G09B 5/12 434/353 |
| 2016/0180248 A1 * | 6/2016 | Regan | G06F 17/30 706/12 |

OTHER PUBLICATIONS

United States Notice of Allowance issued in U.S. Appl. No. 14/180,885 dated Oct. 21, 2015.
United States Non-Final Office Action issued in U.S. Appl. No. 14/180,885 dated Jun. 12, 2015.

(56) References Cited

OTHER PUBLICATIONS

United States Non-Final Office Action issued in U.S. Appl. No. 14/181,058 dated Dec. 4, 2015.
United States Non-Final Office Action issued in U.S. Appl. No. 14/181,016 dated Nov. 6, 2015.
Supplemental European Search Report mailed Aug. 23, 2016 in European Application No. EP 14 751 441, 8 pages.
"Voxy Makes Learning a Part of Your Life", Jan. 24, 2013, pp. 1-5, XP055295304, Retrieved from the Internet: URL://https://web.archive.org/web/20130124031935/http://voxy.com/tour/.
"One-size-fits All Does Not Work for Language Learning", Jan. 24, 2013, pp. 1-4, XP055295282, Retrieved from the Internet: URL://https://web.archive.org/web/20130124031932/http://voxy.com/proven-approach/.
European Communication pursuant to Rules 70(2) and 70a(2) EPC, dated Sep. 9, 2016 in European Application No. 14751441.8, 1 page.

\* cited by examiner

GUI Screenshot 500

Reading Comprehension Task
GUI Screenshot 600

Vocabulary Activity
GUI Screenshot 700

SYSTEMS AND METHODS FOR CALCULATING TEXT DIFFICULTY

CROSS-REFERENCE TO RELATED APPLICATIONS

This application claims priority to U.S. Provisional Patent Application Ser. No. 61/765,105, filed Feb. 15, 2013, which is incorporated by reference in its entirety.

FIELD OF THE DISCLOSURE

The subject matter disclosed herein relates generally to computer-assisted language learning.

BACKGROUND

Conventional language learning methodologies organize learning material into lessons, which may often contain metalinguistic instructional information followed by educationally-oriented exercises. Having pupils demonstrate their knowledge of particular subject matter in various educational activities comprising some series of questions is known. Also known are educational activities in which pupils demonstrate their knowledge by engaging in various tasks. In many cases, educational software may implement educational activities in which pupils demonstrate their knowledge through a series of questions or by engaging in various tasks.

Learning activities are ordinarily prepared manually by a teacher, textbook author, or other curriculum planner. Learning activities are commonly prepared by an instructor, educational expert, or some other party who is preparing educational content and who is also familiar with aspects of language learning. Typically, once these learning activities are generated they are then reproduced en masse. Similarly, conventional distance learning programs rely on prepackaged language learning software or traditional textbooks. In such prepackaged software and textbooks, curriculum planners create content and then try to have the same content serve many people. A problem with this paradigm is that learning activities are not dynamically generated to suit the needs of a language learner.

Conventional language-learning software and tools employ a teaching methodology, curriculum, and coursework that will remain static unless a replacement or supplemental textbook or language learning product is purchased by a language learner or developed by an instructor. Not only is a curriculum not adaptable but, with each page or new computer assignment, there is no adaptability of activities and learning materials on a more granular scale. The overall curriculum is static, so daily activities and skills exercises cannot adapt to address the learner's needs. For example, a learner's past tense verb conjugation may not be a problem, but the learner's spelling may be weak.

Conventional language methodologies often implement distractors, which are pre-determined incorrect answers to academic questions, such as multiple-choice problems. However, conventional language learning methodologies implement distractors that are entirely static and cannot adaptably address learners' weaknesses of particular skills. Moreover, known language learning tools are not adaptable to suit a learner's goals or content preferences. Learners are left to work with the static language learning materials supplied to them, regardless of learners' personal interests or the real-life applicability of the those materials in the context of the learners' goals.

What is needed is an efficient and effective way to dynamically create content and learning materials, or learning activities, for a language learning course. What is also needed is a way to dynamically generate learning activities and language learning coursework that may even adapt automatically mid-course, to suit a language learner's needs, goals, and interests.

As discussed above, developing distractors for the purposes of language learning is known in the art. However, distractors are commonly prepared in some wrote or manual manner so that they may be reproduced in volume. In many cases, when developing learning activities based upon a certain text, the activities must focus on some set of words to exercise various learning objectives. Usually, a person preparing learning activities manually identifies and develops the words upon which learning activities will be based or focused.

What is needed is a way, in a language learning context, to automatically identify words in text, which may be useful to language learning, and then extract those words from text. What is needed is a way to extract useful words of text, or keywords, and then store those keywords for use in developing learning activities.

Identifying keywords in a text to generate a summary of the content of the text is known. Conventional keyword extractors are typically interested in obtaining a percentage of keywords to provide a summary of the text as efficiently as possible. For efficiency, conventional keyword extraction tools seek to summarize the content of the text using as few keywords as possible. But, such conventional keyword extraction tools may incidentally filter out keywords that would otherwise be helpful for language learning, rendering conventional keyword extraction tools ineffective to language learning contexts.

What is needed for language learning is a way to obtain many keywords from text, regardless of whether keywords appear inefficient in summarization contexts. What is also needed is a way to extract and store keywords that are useful for language learning.

There are known means for identifying various attributes of a word in text, e.g., noun, past-tense, first-person, etc. It is also known to filter out various inconsequential words from a line of text. For example, it is known to remove articles such as "the" or "a" from an online search query through the use of a stop word list. Conversely, words which are rare in a corpus, having a lower probability of occurring in a given document, can be given weight in an information retrieval system through known techniques such as TF-IDF.

What is needed is a means for identifying and quantifying the pedagogical value of keywords extracted from text for language learning. What is needed is a way to look at a word's attributes to determine whether the word may help a pupil learn a language.

There are known methods in the art for calculating text difficulty. Conventional methods for calculating the difficulty of a corpus are directed toward adult native language speakers. Conventional methodologies of calculating text difficulty is usually done holistically by teachers and textbook writers. But, there is no established method of calculating a text difficulty that is tailored for second language learners. For native-language readers, and for children learning to read in their first language, there are accepted benchmarks determining text difficulty. There are known systems of qualifying books on levels, such as leveled readers from A-to-Z, something that most schoolchildren learn while learning to read.

Moreover, there are many known readability scales, such as Flesch-Kincaid, which measures the number of words in a sentence and the number of words total. But, known text difficulty calculation methods are designed for learners who already speak the language that they are then learning to read. When teaching a second language to non-native speakers, particularly young adults and adults—many of whom already know how to read in their native language, but simply do not know how to read in the second language—there are different challenges that make reading texts in the second language difficult for them when compared to the schoolchildren learning their native language.

Known first-language text difficulty levels and calculations are not always applicable in situations of adult second-language learners, or non-native speakers. First-language learners are learning to read as a skill, and learning to read is something that takes years, whereas second-language learners typically know how to read in their native language.

What is needed is a means of learning a language that applies a means different from known means of learning a native language. Typically schoolchildren are learning that the word "ball" maps to the concept that they already have for the entity, a ball. Adult language learners, on the other hand, already know how the words may map to certain concepts. So rather than having them start with "that is a ball," adult language learners could start with something inherently more complicated, like "that is an electron," or "I'll take a half-caff latte with organic soy milk." Adult second-language learners typically know how to read complicated items in their own languages. It is desirable for the adult learner to understand these items in a second-language.

Known text difficulty calculation methods may measure text difficulty in comparison to native speakers through their development from childhood. For second-language learners the scale should be different. For example, a non-native speaker may review a long block of text containing very complicated ideas in the second-language, but he or she will have no problem understanding the concepts. This is particularly true if the text contains complicated ideas but is written in a way that exercises simplified language. The ideas are no less complicated. On the other hand, a simple concept like the weather forecast may incomprehensible for a novice language learner if it is written in a linguistically challenging way. This is because the issues second-language learners have are not the same as first-language learners.

What is needed is a way to calculate a text difficulty of a corpus for non-native speakers. What is needed is a way to calculate a text difficulty of a corpus that is more suited for adult language learners. Text difficulty must be calculated primarily according to the idiosyncrasies of the language that make learning that language difficult. What is also needed is a way to automatically determine the appropriateness of text based on the calculated difficulty to then automatically prepare language learning coursework.

Generating distractors for educational exercises is known in the art. Distractors are ordinarily written manually by humans to prepare for various forms of language learning materials, such as a textbook or problems that exercise skills. Afterwards, the attendant language learning materials can the be reproduced en masse. Usually, a teacher or other curricula expert writes questions about the form or content of a resource and then comes up with answers. This means that the teaching methodology, curriculum, and coursework will remain static unless a different textbook or language learning product is purchased. This manual effort is also inefficient and costly.

What is needed is a way to dynamically generate distractors for language leaning. What is needed is a way to adapt distraction generation and selection based on learner's needs. What is needed is a way to automatically generate distractors from a resource. What is also needed is a way to prepare distractors that may adapt to the various types of resources (e.g., a document containing text, an audio playback, a video playback) used for preparing learning exercises.

SUMMARY

The systems and methods described herein include various natural-language processing product features that can be combined with custom-designed learning activities to offer a needs-based, adaptive learning methodology. The system may receive a resource, extract keywords relevant to non-native language learners, assign a difficulty score to the resource, generate a definition as well as a list of potential distractors for each keyword, and topically tag the resource against a taxonomy based on the content. This output is then used in conjunction with a series of learning activity-types designed to meet learners' language skill needs to create dynamic, adaptive activities for them. Various components of the systems and methods are described in further detail below.

In one embodiment, a computer-implemented method of language learning comprises selecting, by a computer, from a resource store a resource having content, wherein the selected resource is related to a content interest of a learner and has a resource difficulty level based upon a proficiency level of the learner; identifying, by the computer, in a user data store that stores one or more abilities of the learner for specific language skills; identifying, by the computer, a specific language skill for improvement based upon the one or more abilities of the learner; identifying, by the computer, a type of learning activity that exercises the identified language skill for improvement; identifying, by the computer, a set of one or more distractors of a type suited to the identified type of learning activity and having a distractor difficulty level based upon the ability of the learner in the specific language skill; generating, by the computer, a learning activity of the identified type of activity utilizing at least one of the set of one or more distractors; updating, by the computer, the ability for the specific language skill in the user data store according to a result from the learning activity; and updating, by the computer, the proficiency level of the learner in the user data store.

In another embodiment, a computer-implemented method for facilitating language learning comprises identifying, by a computer, a particular language skill to exercise; selecting, by the computer, a learning activity that exercises the identified language skill; selecting, by the computer, a set of one or more distractors each of a type of distractor suited to the selected learning activity, wherein each of the one or more distractors are associated with a resource; and generating, by the computer, the selected learning activity, wherein the selected learning activity comprises at least one distractor from the selected set of one or more distractors In another embodiment, a computer-implemented method for crafting a language learning pedagogy comprises: identifying, by a computer, a set of one or more learner capabilities of a learner comprising a language proficiency level and one or more abilities at specific language skills; identifying, by the computer, a set of one or more learner preferences associated with the learner comprising one or more learner content interests; determining, by the computer, a type of learning activity for exercising a language skill based on an ability of the learner at the language skill; determining, by the computer, a set of one or more distractors associated with a resource to implement in the learning activity according to the determined type of activity, wherein a distractor difficulty comparable to the one or more capabilities of the learner; generating, by the computer, the learning activity of the activity type, wherein the learning activity comprises the set of distractors; and generating, by the computer, a lesson comprising a set of one or more learning activities according to a learner goal in the learner preferences.

In another embodiment, a computer-implemented method for tailoring language-learning to a learner comprises: determining, by a computer, an ability of a learner in a specific language skill based on a result of a skill assessment performed by the learner; determining, by the computer, a language proficiency level of the learner based on at least one language skill ability of the learner; receiving, by the computer, a learner content interest and a learner goal from the computing device of the learner; and storing, by the computer, a learner profile associated with the learner in a user data store, wherein the learner profile comprises one or more language skill abilities of the learner, the language proficiency level, the learner content interest, and the learner goal.

In another embodiment, a language learning system for automatically generating activities comprises: a host computer comprising a processor executing a set of software modules for language learning; a keyword store storing a set of keywords extracted from a resource by a keyword extractor module in the set of software modules executed by the host computer; a user data store storing data associated with a learner in a learner profile, wherein the learner profile comprises a set of learner language abilities and a set of learner preferences; and a learner computer comprising a processor configured to execute a user interface to interact with a set of learning activities generated by a learning activity generator module executed by the host computer, wherein a learning activity is automatically generated using the capabilities and preferences of the learner stored in the learner profile.

In one embodiment, a computer-implemented method for extracting keywords from text comprises: parsing, by a computer, a set of one or more potential keywords from text of a resource containing text; storing, by the computer, into a keyword store each potential keyword in the set matching a term in a computer file containing a keyword whitelist and each potential keyword in the set matching a collocation in the keyword whitelist; determining, by the computer, for one or more potential keywords in the set of potential keywords, a word difficulty value associated with each of the one or more potential keywords based on scoring rules determining the word difficulty value; and storing, by the computer, into the keyword store each potential keyword having a determined pedagogical value that satisfies a threshold word difficulty value.

In another embodiment, a system comprising a processor and non-transitory machine-readable storage containing a keyword extractor module instructing the processor to execute the steps of: parsing text from a resource into a set of one or more potential keywords; identifying one or more collocations in the set of potential keywords matching a collocation in a file containing a keyword whitelist; determining a pedagogical value for each extracted word according to one or more scoring rules; and storing a set of one or more extracted keywords into a keyword store, wherein the set of extracted keywords comprises each potential keyword having a word difficulty value satisfying a threshold value and each identified collocation.

In one embodiment, a computer-implemented method for predicting a text difficulty score for a new resource comprises extracting, by a computer, one or more linguistic features having a weighted value from a plurality of training resources containing text, wherein the text is associated with a metadata label containing a text difficulty score of the text; determining, by the computer, a vector value associated with each training resource based on each of the weighted values of each of the extracted one or more linguistic features; training, by the computer, a statistical model using the vector values associated with each training resource, wherein the statistical model represents a correlation between a set of features selected for extraction, a set of weighted values assigned to the set of features selected for extraction, and a set of text difficulty scores associated with the training resources; extracting, by the computer, one or more linguistic features having a weighted value from a new resource; determining, by the computer, a vector value for the new resource based upon the set of extracted linguistic features; and predicting, by the computer, a text difficulty score for the new resource based upon the vector value for the new resource and the statistical model.

In another embodiment, a computer-implemented method for determining text difficulty for a resource comprises: comparing, by a computer, at least a portion of text related to a resource against a lexical feature bank file comprising a listing of semantic features and a listing of syntactic features; identifying, by the computer, a set of lexical features associated with the text based on the comparison, wherein the set of lexical features comprises at least one semantic feature from the text matching a semantic feature in the list and at least one syntactic feature from the text matching a syntactic feature in the list; assigning, by the computer, a first value to each of the lexical features in the set of lexical features; and determining, by the computer, a text difficulty score for the text using each of the first values associated with each of the features in the set of lexical features.

In another embodiment, a system comprising a processor and non-transitory machine-readable storage containing a text difficulty calculator module instructing the processor to execute the steps of: comparing text in a resource against a listing of features comprising a list of semantic features and a list of syntactic features; identifying one or more semantic features in the text matching the listing of features, and identifying one or more syntactic features in the text matching the listing of features; assigning a value to each of the identified semantic and syntactic features in the text according to a statistical model, wherein the statistical model identifies the value associated with each feature in the listing of features; and determining a text difficulty score associated with the resource using each of the values assigned to the identified semantic and syntactic features.

In one embodiment, a computer-implemented method for facilitating language learning comprises: generating, by a computer, a set of one or more semantic distractors comprising one or more words having a definition that is related to a target word; generating, by the computer, a set of orthographic distractors comprising one or more words having an edit distance satisfying an edit distance amount setting, wherein the edit distance is a number changes to a word required to be identical to the target word, and wherein the edit distance amount setting determines the number of changes to the word; and generating, by the computer, a set of phonetic distractors comprising one or more homophones of the target word.

In another embodiment, a system comprising a processor and non-transitory machine-readable storage containing a distractor generator module instructing the processor to execute the steps of: receiving one or more keywords extracted from a resource containing text; identifying in one or more dictionary sources, one or more distractors that are of one or more distractor types and are associated with a keyword; and generating a set of one or more identified orthographic distractors comprising a word having a predetermined edit distance relative to the keyword.

Additional features and advantages of an embodiment will be set forth in the description which follows, and in part will be apparent from the description. The objectives and other advantages of the invention will be realized and attained by the structure particularly pointed out in the exemplary embodiments in the written description and claims hereof as well as the appended drawings. It is to be understood that both the foregoing general description and the following detailed description are exemplary and explanatory and are intended to provide further explanation of the invention as claimed.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

DETAILED DESCRIPTION

Figure 1:
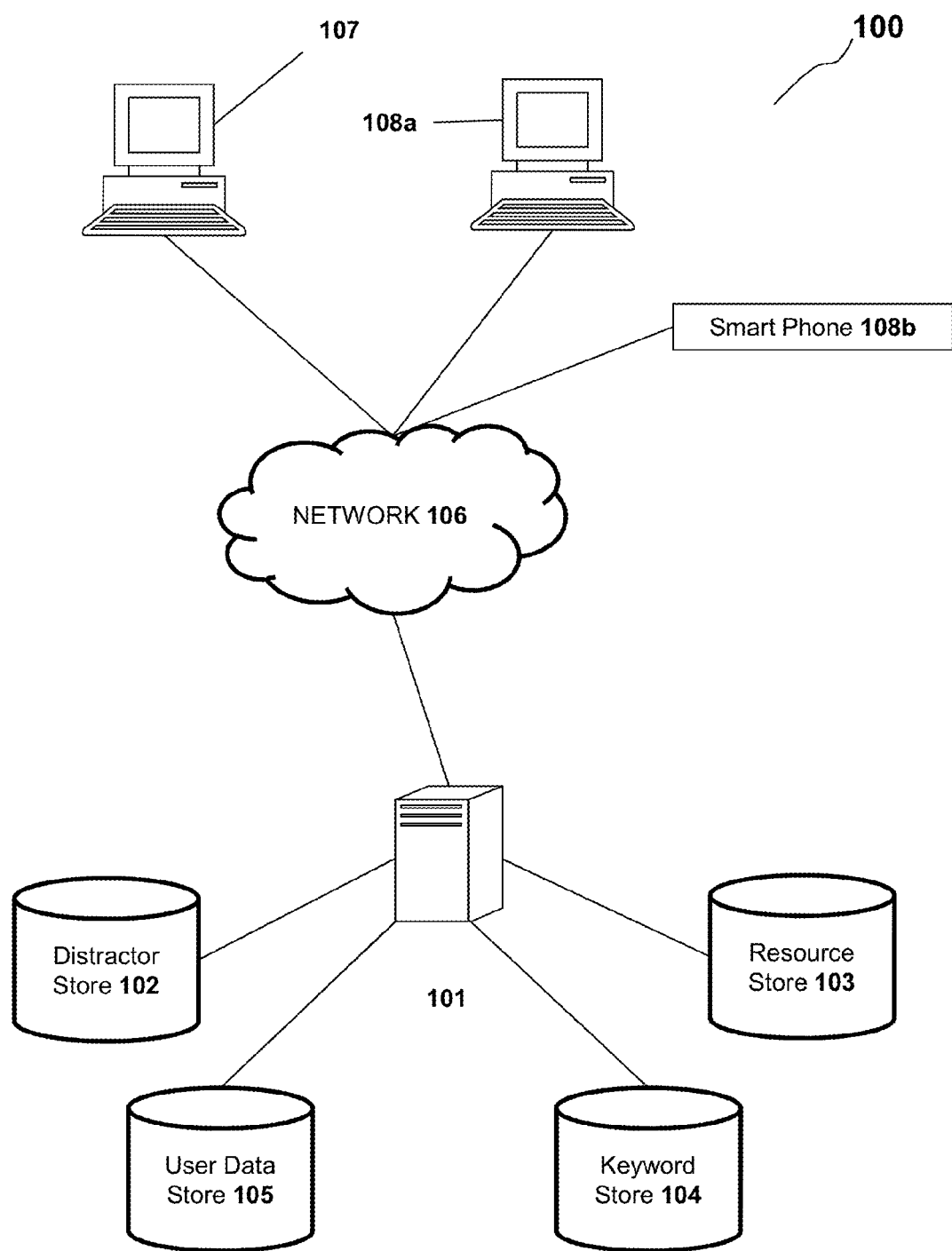
FIG. 1 shows an exemplary embodiment of a language-learning system.

The present invention is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

Embodiments of the system may automatically develop one or more portions of a series of learning activities of various intended learning outcomes, e.g., improved vocabulary, improved reading comprehension, improved overall learner proficiency. Learning activities may pull data automatically generated by various software modules that are executed on one or more computing devices, and/or data of various types stored in a resource store.

Modules generating data may be a keyword extractor, a distractor generator, and a text difficulty calculator. The various components of the language learning system may develop output used by a learning module as input for portions of lessons generated by the learning module. Thus, the learning module may dynamically create learning activities suited for language learners based on a variety of resources.

In some embodiments, learning activities may use as input various information describing aspects of the language learner such as a learner's interests, the learner's overall language proficiency level, and/or the learner's abilities in various particular language skills. For example, a resource used for a learning activity may be selected based on the learner's interest in sports. As another example, the learning activity may be generated to exercise a particular language skill where the learner needs to focus, which is determined according to an assessed ability in that particular skill (e.g., spelling, reading comprehension). In another example, a more rigorous or well-rounded set of learning activities may be generated if the learner has a goal to prepare for the TOEFL as opposed to preparing for a vacation.

Resources selected to use in building learning activities may vary in difficulty, type, and content. For example, resources may be linguistically difficult or easy, relative to one another and/or relative to learners' proficiency levels. As another example, resources may be one or more portions of text of a document or transcript, audio, video, audiovisual, or images.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are considered within the scope of the invention.

Language Learning System Components

FIG. 1 shows the components of an exemplary embodiment of a language-learning system 100.

The language learning system 100 of FIG. 1 comprises a language learner server 101, a distractor store 102, a resource store 103, a keyword store 104, a user data store 105, a network 106, a content curator computer 107, and language learner's computing device 108. As shown in this exemplary embodiment, a language learner's computing device 108 may be a language learner's computer 108*a* or a language learner's smart phone device 108*b*.

A language learner server 101 may be any computing device, such as a personal computer, or any other computing device comprising a processor that may be capable of executing one or more language learning modules. Embodiments of the language learning server 101 may comprise a keyword extractor module, a text difficulty calculator module, a distractor generator module, and/or a learning module.

In the exemplary embodiment the language learning system 100 in FIG. 1, the language learner server 101 is shown as a single device. However in some embodiments, the language learner server 101 may comprise multiple computing devices. In such distributed-computing embodiments, where a language learner server 101 comprises a plurality of computing devices, each of the computing devices may comprise a processor. And each of these processors may execute language learning modules that are hosted on any of the plurality of computing devices.

Embodiments of the language learning system 100 may comprise one or more data stores 102, 103, 104, 105: a distractor store 102, a resource store 103, a keyword store 104, and a user data store 105. Data stores 102, 103, 104, 105 may be databases comprising non-transitory machine-readable storage medium storing and retrieving data related to one or more modules executed by a device processor in the language learner server 101. Data stores 102, 103, 104, 105 may be a single device hosting the database, or data stores 102, 103, 104, 105 may be distributed among a plurality of computing devices hosting databases.

In some embodiments of a language learning system 100, one or more of the distractor store 102, the resource store 103, the keyword store 104, and/or the user data store 105 may reside on a language learner server 101. In some embodiments, such as the one shown in FIG. 1, the language learning server 101 is a single device and each of the data stores 102, 103, 104, 105 are hosted on distinct devices, each communicating with the language learner server 101. An ordinary artisan would appreciate that data stores 102, 103, 104, 105 may communicate with the language learner server 101 over any number of communication means capable of facilitating networked communication between computing devices, e.g., LAN, WAN, InfiniBand, 3G, 4G, or any other computing communication means.

A distractor store 102 may be non-transitory machine-readable storage medium storing one or more distractors that are related to keywords. The stored distractors may be dynamically generated by a distractor module executed by a language learner server 101.

A resource store 103 may be a non-transitory machine-readable storage medium storing one or more resources. Resources may be received from a content curator device 107, a learner computing device 108, or another external data source, such as a website, blog, or news service. A resource stored in the resource store may be one or more portions of text of a document (e.g., book, article, webpage, journal), an audio output, a video output, an audiovisual output, an image, or a combination thereof. In some embodiments, a resource store 103 may also store metadata associated with stored resources. Non-limiting examples of metadata may include information describing a text difficulty score for text in a document resource, the length of a resource, and/or the content contained in a resource.

In some embodiments of the resource store 103, resources may be multimedia resources (e.g., audio, video, image). In such embodiments, the resource store 103 may store metadata related to a stored multimedia resource. For example, the textual transcript of an audio or audiovisual resource may be stored in the resource store 103 as associated metadata. As another example, metadata may contain one or more timestamps that correspond to particular timing points in a video or audiovisual resource. Timestamps may be associated with a transcript or a other descriptive text of the resource, e.g., a keyword in view at particular timing point, or a description of events. In another example, metadata may contain descriptions of points (e.g., coordinates) for bounding boxes encompassing areas of an image resource. Some embodiments have multimedia resources, metadata may identify one or more keywords in the multimedia resources. This metadata may correspond with keywords in a keyword store.

In some embodiments of the resource store 103, metadata related to multimedia resources may be manually entered by a content curator using a user interface of a content curator device 107. In some embodiments, resources may be automatically retrieved from a variety of external sources or received from external sources on a regular basis. In these embodiments, metadata associated with multimedia resources may be automatically retrieved, received, or updated, from the external source promulgating the associated resource. In some embodiments, the metadata may be retrieved from various external sources storing data related to multimedia resources already stored in the resource store 103.

A resource store 103 may store resources transmitted from a user interface of a computing device 107, 108 within a language learning system 100 or from some external data source. The resource store 103 may execute search queries to search the resource store 103 for resources. These search queries may be received from language learning modules executed by a language learning server 101, or from a computing device 107, 108.

A keyword store 104 may store one or more keywords extracted from resources. A keyword store 104 may store metadata associated with the keywords, such as their originating resource from which they were extracted, or a word difficulty score describing linguistic difficulty of the keyword. A keyword store 104 may receive and store keywords from a keyword extractor module that is executed on a language learner server 101. A keyword store 104 may also store keywords input from a user interface of computing device 107, 108. A keyword store 104 may execute search queries to search for a keyword according to queries received from language learning modules executed by a language learning server 101.

A keyword store 104 is a computer-readable storage medium that may store keywords, keyword attributes, and/or various other means for retrieving data stored in the keyword store 104, such as an offset or a unique database record key. In such embodiments of the keyword extraction module, the keyword extraction module proceeds to store certain potential keywords into a keyword store 104, as keywords extracted from a corpus or resource. Various algorithms and/or other operating rules instructing the keyword extraction module may be used to determined which of the keywords are to be stored into the keyword store 104.

A user data store 105 is non-transitory machine-readable storage medium that may store learner profiles containing information related to language learners. A user data store 105 may receive and store data from one or more language learner modules executed on a language learner server 101, or a user data store 105 may store data input from a user interface of a computing device 107, 108. A user data store 105 may execute search queries to search for learner profiles according to commands received from one or more language learning modules executed by a language learning server 101.

A network 106 may connect each of the computing hardware devices in the language learning system 100 to one another. One having ordinary skill in the art would appreciate that there are many possible permutations for connecting the various devices and components in embodiments of a language learning system 100. Embodiments of a network 106 may facilitate hardware components of a language learning system 100 to be proximately located within a building, a campus, a municipality, or across any geographic span.

As seen in the exemplary embodiment of a language learning system 100 shown in FIG. 1, a network 106 may be a combination of public network, such as the Internet, and private networks. However, in some embodiments, the network 106 may only be a private network, or only a public network. The network 106 of FIG. 1 represents a combination of the Internet and some internal private network. The network 106 may be a mixture of various data communication technologies, i.e., LAN, WAN, and 4G.

In some embodiments, a network 106 may only connect some of the hardware components of a language learning system 100 while some other hardware components are connected with the language learning system 100 using different technologies or a different network. For example, data stores 102, 103, 104, 105 of FIG. 1 may communicate with the language learning server 101 using, for example, InfiniBand, for proximately located devices. Moreover, in some embodiments one or more of the components may reside on a single device.

An ordinary artisan would appreciate that a language learning system 100 may be a distributed computing system using one or more networking technologies and redundancies technologies that may employ a number of known underlying techniques for facilitating communication between computing hardware components.

One having ordinary skill in the art would appreciate that the networking architecture shown in the embodiment of the language learning system in FIG. 1 does not in any way limit architectural permutations facilitating communications between various components of other embodiments of a language learning system 100.

A content curator computing device 107 may be a computer, smart phone, server, a tablet, a gaming system, or other computing device comprising a processor configured to implement a user interface to administer the various modules and components of a language learning system 100. In some embodiments, the content curator computing device 107 may be capable of networked communications with various other computing devices.

Embodiments of a content curating device may execute a user interface that may allow a content curator to review output from, and/or manually input various pieces of information, resources, and/or metadata into the modules executed by the language learning server 101, or into data stores 102, 103, 104, 105 within the language learning system 100.

For example, in some embodiments, a content curator may store a resource in a resource store and then manually enter curated metadata that is associated with the resource, such as a timestamp for a video resource or a transcript for an audio resource. The content curator computing device may attach metadata to resource for associating the resource with a keyword or identifying various other attributes of the resource. In some embodiments, a content curator computing device may receive information associated with a learner or input data into a user profile associated with a learner. The information or data may be received from a content curator inputting the information or data on a user interface associated with the content curator computing device.

In some embodiments, a content curator computing device 107 may allow a content curator to act as a tutor in either live chat, telephonic, and/or video sessions with a learner's computing device 108, or in correspondence, e.g., e-mail. It is to be appreciated that a content curator computer 107 may be a computing device networked to communicate with a language learner server 101. However, a content curator computer 107 may also be the same device as the language server 101.

A learner computing device 108 may be a computer 108a, a smart phone 108b, a server, a tablet computing device, a gaming system, or any computing device having a processor configured to implement a user interface to communicate with the various modules of the language learning server. It is to be appreciated that a learner computer 108a may be networked to communicate with a language learner server 101, but a learner computer 108a may also be the same device as the language server 101.

In some embodiments, a learner computing device 108 may engage into a tutoring session with a content curator device 107 over a network 106. The tutoring session may be held over any video-calling technology, voice call technology, or instant messaging service, such as Google Hangouts®, Skype®, VoIP, and/or instant messaging software. In some embodiments, this tutor session may not be a product of a third-party vendor, and is instead native to the language learning system 100. In other embodiments, the language learning system 100 may comprise a tutor messaging service for the tutor and the learner to message one another outside of a tutoring session.

A learner computing device 108 may send and receive electronic messaging within the language learning system 100 or through conventional messaging services. A content curator computing device 108 may likewise facilitate such communication tutoring between a content curator and learner. A content curator device 108 may also include an interface for generating tutoring assignments, grading assignments, scoring learning activities, and sending/receiving assignments with a learner. These assignments may be sent through the native messaging service or through the conventional messaging service.

In some embodiments, learners may take an initial proficiency assessment. This assessment may be a test or quiz stored on the language leaning server 101. The assessment may be presented to learners through the user interface of the learner's computing device 108. The assessment may be scored automatically by the language learning server 101, or may be scored by a content curator using the computing device of the content curator 107. This assessment may provide an initial global learner proficiency score and/or scores reflecting the learner's abilities in particular language skills, which are stored in a user data profile. The proficiency level and/or language skill abilities of the learner may be automatically updated in the user data store 105. The modules of the language learning server 101 may automatically update the user data profile in the user data store 105 based on the learner's performance in learning activities, and in some embodiments, learners may take a periodically recurring proficiency assessment through a learner's computing device 108 to level-up in proficiency level or in an ability score.

Keyword Extractor

When applied in a language learning context, a keyword extractor as described herein may address shortcomings of conventional keyword extractors since conventional keyword extractors are not commonly applied to language learning. The goal of conventional keyword extractors is to save a human reader time by reducing the number of words they need to read to extract meaningful information from the resource. These algorithms are optimized for finding the smallest subset of words which have a high information content, which results in the filtering out of common words, phrases, idioms and other vocabulary which lies in a more general topic domain. Embodiments of the keyword extractor described herein implement keyword extraction techniques for extracting keywords useful for language learning. Conventional keyword extraction techniques are not applied in context of language learning and as such, conventional keyword extraction can be ineffective.

Embodiments of a language learning system may include a keyword extractor, otherwise referred to as a keyword extraction module, which is a component embodied on a computer-readable medium and executed by a processor. The keyword extractor may obtain one or more keywords from text. Keywords may be a particular word or set of words (e.g., phrase, collocation) recited in a resource.

Conventional keyword extraction techniques merely extract enough words to summarize the content conveyed by text. However, embodiments of a keyword extraction module described herein may be executed to gather as many keywords as needed to facilitate language learning using a particular document or set of documents. The keyword extractor may implement keyword extraction techniques adapted for language learning, which requires different information content identification and extraction heuristics. For example, a word which may not be closely connected to the meaning of a text would be discarded by conventional keyword extractors. However, this word may still have pedagogical value to a language learner at a lower level of proficiency where general vocabulary is being acquired.

As described herein, a keyword extraction module may, among other features, extract keywords from a resource that are pedagogically valuable to language learning. Pedagogically valuable keywords may be words in the text of a resource containing text, such as a document (e.g., article, journal, blog) or a transcript, which may aid language learning due to certain attributes or aspects associated with those words. As an example, a keyword may be pedagogically value when the keyword is easily defined or when the keyword is central to the context of the resource.

Embodiments of an extraction module may implement a keyword whitelist as a way of determining pedagogical value of potential keywords parsed from text. A whitelist may be any type of computer file containing words predetermined to be keywords to extract. In such embodiments, a keyword whitelist may comprise words that are automatically stored into the keyword store as an extracted keyword.

In some embodiments, a stop word file may be any computer file containing words that are never keywords for extraction. The stop word file may act as a filter against words that are not particularly advantageous to language learning.

In some embodiments, the keyword extractor module may implement one or more scoring rules, which may be one or more algorithms for determining pedagogical values of potential keywords. It is to be appreciated that multiple whitelists and stop word files may be used, or the whitelist and stop word file may be the same single computer file.

Figure 2:
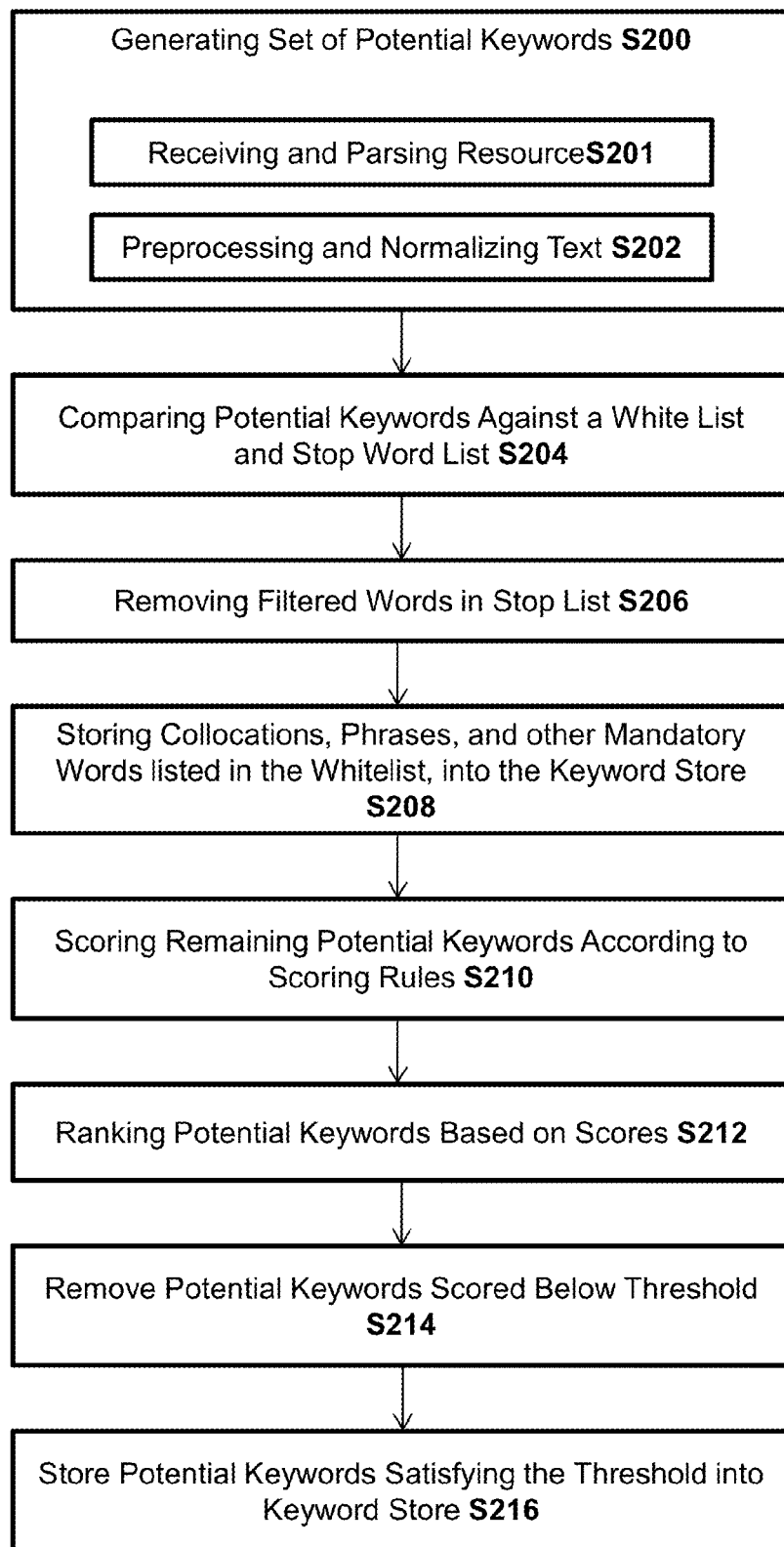
FIG. 2 shows a flowchart for an exemplary method embodiment of keyword extractor module.

FIG. 2 is a flowchart for a method embodiment of keyword extraction from the text of a resource.

In step S200, after receiving a resource containing text, a keyword extraction module may begin the process of keyword extraction in step by generating a set of potential keywords. In some embodiments, step S200 may begin with a step S201 in which the keyword extraction module receives a resource and then parses the text of that resources into a resulting set of potential keywords. Step S200 may optionally utilize a step S202 in which a keyword extraction module begins generating a set of potential keywords by preprocessing and/or standardizing the text parsed from the resource.

In a next step S204, embodiments a keyword extraction module may compare the set of potential keywords against a keyword whitelist to determine whether each potential keyword is pedagogically valuable.

Based on the comparison in step S204, in a next step S206, a keyword extraction module removes potential keywords, from a set of potential keywords, that match a filtered word listed in the stop word file.

Embodiments of a keyword extraction module may implement a stop word file that may filter out words pre-identified as lacking pedagogical value. Non-limiting examples of stop words that are filtered out of the set of potential keywords may include: ordinal numbers, numbers, proper nouns, and/or conjunctions.

In a next step S208, the keyword extractor module may store potential keywords matched to a word in the keyword whitelist file identified as having pedagogical value for language learning. Non-limiting examples of such words may include collocations, verbal phrases, words or phrases identified as difficult for non-native speakers, words related to the resource, and/or words pre-identified as words critical to the language being learned.

A keyword whitelist file may identify one or more collocations as having pedagogical value, each of which may be kept as an extracted keyword. Collocations are words frequently found together in texts, such as "put out." Language learners typically learn such collocations in chunks. But, conventional keyword extraction tools typically eliminate collocations arising in a document. Embodiments of the keyword extractor may be adapted to specifically look for such collocations.

In a non-limiting example using "put out," there may be circumstances where the term "put" may otherwise be filtered out as lacking value, but phrasal verbs such as "put out," "put up," or "put on" might be recognized as collocations and, as such, they may be extracted by the keyword extraction module. Language learners must learn each of these usages of the word "put" because each of these instances of the term "put" have different meanings, and are equally distinct from the word "put." In this example, the keyword extraction module facilitates teaching a language learner each of these sets of collocations and various usages of the term "put." Thus, language learners may see the difference between "put on," rather than only the term "put."

Continuing with step S208, potential keywords identified by the keyword extraction module as having pedagogical value may be stored in a keyword store. The keyword store is a computer-readable storage medium that may store keywords, keyword attributes, and/or various other means for retrieving data stored in the keyword store, such as an offset or a unique database record key.

Embodiments of a keyword extractor module implement a keyword store may store extracted keywords in the keyword store associated with keys of n-grams, a set of one or more collocations, and one or more offsets. As used herein, the term keyword may refer to a word or phrase comprising one or more words, such as a collocation.

A keyword store stores keywords with keys of n-grams. An n-gram may be a sequence of one or more words, n, recited within a unit of meaning in a text, which may refer to the length of the keyword. In other words, a keyword store may store unigrams, bigrams, and/or trigrams, or more, depending upon the length of the keywords being extracted.

For example, a unigram may be a word of text that stands on its own, thus "dog" is a unigram. Likewise, the phrase "dog walker" is a bigram, and the phrase "dog walking service" would be a trigram. Between each of the three examples of potentially extracted keywords, there is some grammatical connection between three potential keywords. These three examples may be fitted together to form a unit of meaning, i.e., form a set of concepts together.

A keyword store may also store extracted keywords in association with collocations, and/or offsets. Collocations in this context are similar to other database keys in that they may be stored in association with an extracted keyword in the keyword store, these collocation keys represent a subset of one or more collocations reciting the extracted keyword in a resource, recited in an ongoing history of resources, or manually entered by a content curator. Offsets associated with the keyword in the keyword store may be one or more values indicating the start and end positions of the keyword associated with a resource.

After the keyword extraction module generates the set of potential keywords in step S200, the keyword extraction module may store all, or a subset, of the potential keywords, into the keyword store, as extracted keywords. The keyword store may store only the keywords extracted from a resource. Some embodiments may allow this keyword store to build over time, thereby accruing extracted keywords; some of these embodiments may also accrue the extracted keywords and associate them with their respective resources from which the keywords were extracted.

In a next step S210, a keyword extraction module may determine a score for each of the remaining potential keywords, i.e., potentials keywords not already eliminated or stored into the keyword store according scoring rules that evaluate each word's pedagogical value. Embodiments may score potential keywords using various permutations and combinations of algorithms, software, and/or other tools, either known or disclosed herein, to determine the pedagogical value of a word.

As a non-limiting example, a keyword extractor may score bigrams and trigrams using co-occurrence statistics, implemented by using a natural language processing tool, such as the Natural Language Toolkit of the Python scripting language, to determine the likelihood that a word should remain a potential keyword. In this example, the keyword extractor determines the criticality of a word to the text by measuring the word's frequency.

As another non-limiting example, a keyword extractor may refer to a list of collocations specifically configured for English learners at a particular proficiency level.

As discussed later, as another non-limiting example, a keyword extractor may generate an additional word difficulty score to rank words in terms of likelihood of difficulty for non-native speakers to learn and master. Non-limiting examples of parameters used for calculating a word score may include a word's length and/or frequency of which the word's part-of-speech is exercised in a broader population of external corpora, such as a term frequency-inverse document frequency (TF-IDF) score.

Figure 2A:
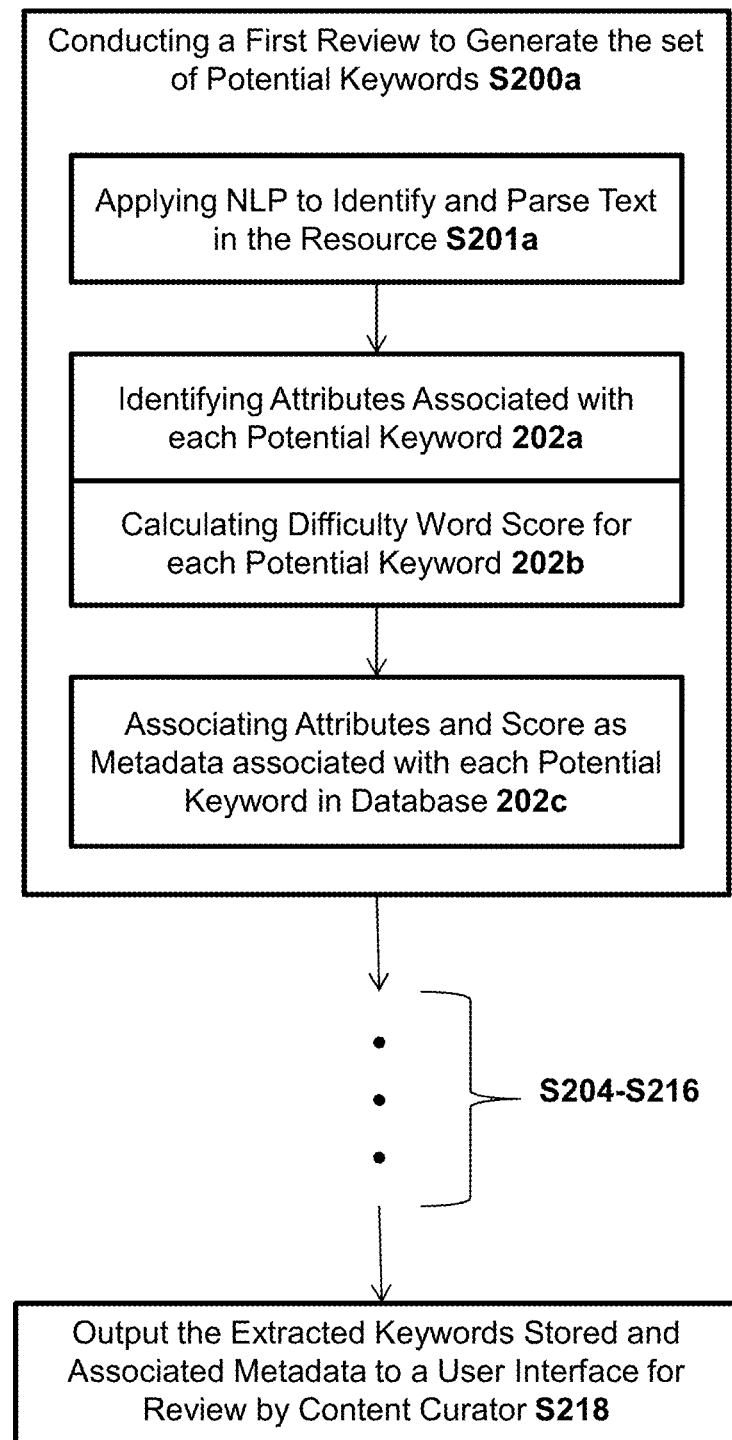
FIG. 2A shows a flowchart for an exemplary method embodiment of keyword extractor module.

As shown in FIG. 2A, the keyword extractor may include an optional first review step S200a and an optional second review step S218.

In a step S200a, a keyword extractor implements a first review step in generating the set of potential keywords. Step S200a may comprise optional steps S201a, S202a, S202b, and/or S202c.

In a step S201a, a keyword extractor may use known natural language processing tools and techniques to generate the set of potential keywords.

In a step S202a, the keyword extractor may implement the natural language processing techniques to identify one or more attributes associated with a potential keyword. In this step the keyword extractor may, for example, automatically identify a word's part-of-speech as a noun, adjective, verb, or otherwise. Other non-limiting examples of attributes that a keyword extractor may automatically identify and associate with potential keywords may include a topic and/or sub-topic for a potential keyword, a number of syllables in a potential keyword, a number of times a potential keyword appears in a resource comprising all of the resources stored in the resource store, one or more resources stored in the resource store, or other external resources or TF-IDF, and/or a definition for a potential keyword.

In a step S202b, a keyword extractor may calculate a word difficulty score for a potential keyword based on factors pulled from attributes associated with the potential keyword. These factors may include, but are not limited to, TF-IDF of the word in the resource store, resource or external sources, a number of syllables in a potential keyword, and whether a potential keyword appears on an Academic Word List (AWL).

In a step S202c, attributes of words may be identified and included in the keyword store as metadata associated with a potential keyword. For example, metadata may include a part-of-speech, an originating resource, a definition of a word, or a context in which an extracted keyword is used in text. A context may be determined using metadata associated with the resource in which a resource's content was identified and stored in a resource store or manually input. The keyword store may store a potential keyword in association with any resource content reciting the potential keyword. Some embodiments of the keyword extractor may implement a tagging system for associating, or tagging, metadata with keywords.

After step S202c, a keyword extractor may perform one or more of the steps between S204 through S216 shown in FIG. 2.

In an optional step S218, a keyword extractor may initiate an optional second review of the text. In this step, each potential keyword and the associated metadata may be presented to a user interface, of a client computing device, operated by a content curator. The content curator may then interact with the user interface to confirm that the keywords, metadata, and/or associated attributes, such as the definitions, are correct in the context of the text. A content curator may further review that the keywords, metadata, and/or associated attributes are appropriate in the context of the text.

Text Difficulty Calculator

Systems and methods of language learning may include a text difficulty calculator module, which is a component of a computer program product embodied on a computer-readable medium and executed by a processor to perform the specified functionality. A text difficulty calculator module may determine a language difficulty for text in a resource.

In some embodiments, a text difficulty calculator may group resources into a plurality of groups or proficiency levels according to difficulty scores. In such embodiments, resource groupings may correspond to proficiency levels assigned to language learners. That is, language learners may be ascribed a proficiency level determining the difficulty of resources in which they are presented for language-learning purposes, e.g., a beginner or first-level language learner may interact with first level resource.

For example, in such embodiments a text difficulty score may identify a resource as having text of minimal difficulty relative to the rest of a corpus comprising one or more other resources stored in a resource store. This relatively easy resource may be grouped with resources having comparable text difficulty scores. The group may now be considered a beginner level, a first level, or other starting level designation.

In some embodiments, the number of groups, and/or the granularity to which resources are segmented into these groups, is the decision of the content curator. In other embodiments, the determination of granularity and/or the number of groups may be automatically determined.

A text difficulty calculator module may analyze the text difficulty of the language in the text using a set of linguistic features. This set of features comprises one or more semantic features and one or more syntactic features. Non-limiting examples of these features may include the difficulty of the words in the text, the manner in which the words are used within the context of the overall text, the overall complication of the content conveyed by the text, and the difficulty of the syntactic construction of the text. Non-limiting examples of difficulty of syntactic construction may include the number of relative clauses in the text, or the distance of pronouns from their related antecedents.

In some embodiments, a text difficulty calculator may identify syntactic and semantic features of the text in a resource. Using the identified syntactic and semantic features as inputs into one or more algorithms, the text difficulty calculator may determine the language difficulty of the text. Some embodiments may implement a clustering analysis to predict the text difficulty of a given resource for particular groups of non-native speakers.

In some embodiments, a text difficulty calculator module must be trained to be capable of identifying features in text and associate weighted values to features. The text difficulty calculator module may receive training resources having text in which various features are found. Training resources may be tagged or labeled with metadata indicating weighted values associated with each of the features in the text, and the resource may be tagged or labeled with metadata indicating the text difficulty score of a training resource.

As an example, the text difficulty module may receive a set of training resources. Each of the training resources is labeled with data indicating the difficulty score, e.g., on a scale from 1-7. For each training resource in the set of training resources, the text difficulty module may then extract a set of linguistic features having a weighted value. So for example, linguistic features in the text of a training resource may be associated with a floating point decimal representation. Taken together, the set of linguistic features identified in a training resource may be represented as a vector of numeric values based on the weighted values of each of the linguistic features. The vector for each training resource in the labeled data set of training resources is then used to train a statistical model for predicting a text difficulty scores of new resources. The statistical model may represent the correlation between the features selected for extraction from resources (e.g., identified in a list of lexical features to extract), the weighted values associated with those linguistic features, and the corresponding labels. When new resources are received, a vector may be determined for the new resource based on linguistic features identified and extracted from the new resource. The vector of the new resource may allow the system to label the new resource with a predicted text difficulty score using the statistical model.

Figure 3:
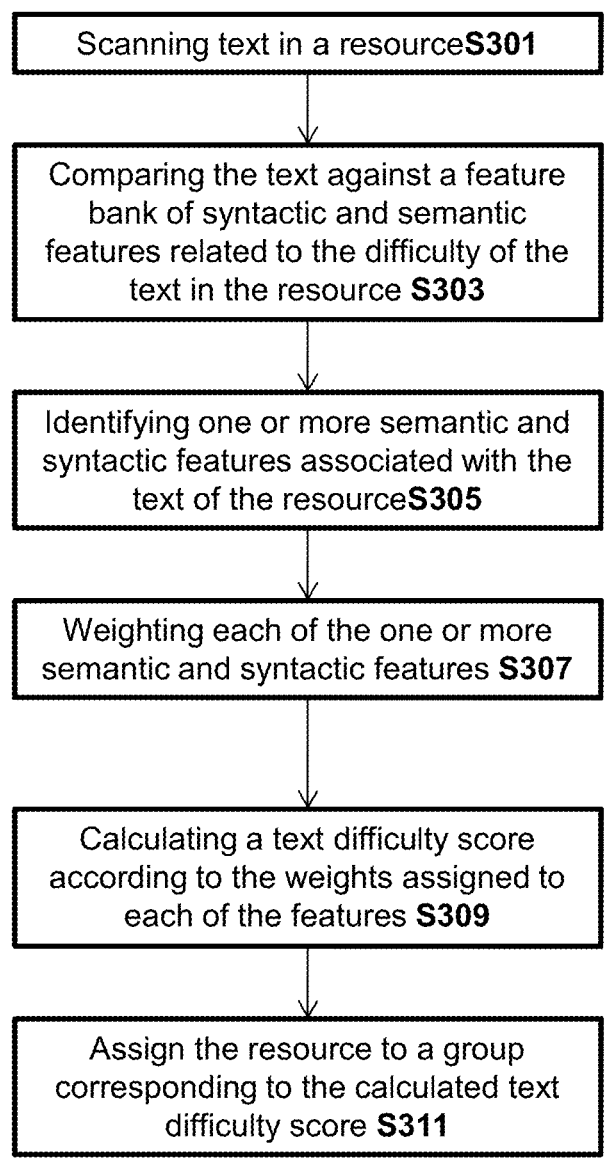
FIG. 3 shows a flowchart for an exemplary embodiment of a method of determining a text difficulty score for language of text.

FIG. 3 shows a flowchart for an exemplary embodiment of a method of determining a text difficulty score for language of text in a resource.

The embodiment of FIG. 3 shows steps S301, S303, S305, S307, S309, and S311. However, a person having ordinary skill in the art would appreciate that other embodiments may vary the steps performed. The embodiment of FIG. 3 scans text to identify syntactic and semantic features of the text, and then uses the identified features as inputs into one or more algorithms to determine the language difficulty of the text.

In step S301, the text difficulty calculator receives a resource containing text and then the text of the resource is scanned for various features, as discussed in a next step S303.

Continuing with step S301, in some embodiments, a resource may be received or fetched from a resource store within a language learning system. In some embodiments, resources of various types may be received from a user interface on client computing device. This user interface may be that of a content curator or a language learner, and the user interface may transmit one or more selected resources to the language-learning system to implement in the various components described herein. Resource received from a user interface may be received by a text difficulty calculator to perform a text difficulty determination.

In some cases, a text difficulty calculator may scan only a portion, or several non-contiguous portions, of text of a resource. For example, the text difficulty calculator may scan only a particular entry of an encyclopedia, without scanning the entire encyclopedia.

In a next step S303, the text difficulty calculator compares scanned text against features listed in a feature bank.

A lexical feature bank may be a computer file containing a listing of semantic features and a listing of syntactic features. The features listed in the feature bank may be used to determine language difficulty of text in a resource. The features in the feature bank describe and correspond to various aspects of texts that make reading or understanding a text difficult for non-native speakers and second-language learners.

In a step next S305, a text difficulty calculator may identify a set of features in the text of a resource based on the comparison with the lexical feature bank in step S303. This set of identified features may comprise semantic features and syntactic features.

Semantic and syntactic features identified in text may be features that make the text difficult to comprehend for language learners. For example, an adult language learner, who is capable of proficient reading comprehension in their native language and also understands concepts map to text, may be learning English. In this example, the learner only needs to learn to read in English, but they do not need to learn that concepts map to the text written in English.

So in this example, semantic and syntactic features identified during the comparison step S303, are features of a text, written in English, that focus on the linguistic aspects of English that makes reading English difficult. Or, the features may relate to concepts in English that make English different from the language learner's native language. Non-limiting examples of this may include negative-polarity items (i.e, terms such as "anyone" or "no one"), which can be unique to English and may be difficult to explain to a non-native language learner. Another example may be a large amount of wh-movement, i.e., relative clauses far away from the terms being modified by the relative clause.

In a step S307, after identifying a set of features in a text, each semantic feature and each syntactic feature in the set of features, are assigned a value or weight, based on a relative difficulty that each feature contributes to the overall difficulty of the text.

In some embodiments of a text difficulty calculator, a lexical feature bank may result from features extracted from a labeled data set of training resources. The lexical feature bank may be a file listing lexical features and is stored in a non-transitory machine-readable storage medium accessible to the text difficulty calculator.

For example, a text difficulty calculator may employ a labeled data set of training resources with pre-identified semantic and syntactic features label with metadata identifying the features in the text. Non-limiting examples of the features may include: lexical frequency of various words (i.e., how often words show up in resources in the resource store corpus or in external corpora); the length of the sentences in the text; the amount of coordination and subordination in the sentences; and the distance between pronouns and antecedents.

As previously mentioned, a labeled data set may be training resources having metadata associated with the semantic and syntactic features in the text of the training resource. In the labeled data set, each of the semantic and syntactic features may be associated a weight corresponding to how much difficulty the particular feature contributes to the overall linguistic difficulty of the text. When an extracted feature of text in a resource is identified as matching a particular feature in the labeled data set, the text difficulty calculator may assign a particular weight associated with the feature as found in the labeled data set.

In some embodiments, a content curator may determine each of the assigned weights. In some embodiments a text difficulty calculator may accept a manual input for each of the weights from a user interface of a content curator. In some embodiments, a content curator may review, revise, and/or update the weights for each of the features. And in some embodiments, the content curator may use the user interface to amend one or more algorithms, such as a logistic regression algorithm, to determine the correct weight for each of the features.

For example, a user interface of a content curator may be used to correct a difficulty score calculated for a particular word, thereby updating a weight automatically associated with a feature or word. As another example, a user-labeled weight (representing difficulty of a feature or word) may be manually entered as a training label to improve accuracy of algorithms (e.g., a statistical model) used to automatically compute the text difficulty score.

In a step S309, a text difficulty score is determined using the assigned weights for each of the features as parameters to one or more algorithms used to determine the text difficulty score. Some embodiments may assign two values as weights, that is a first value is assigned and then a second value may again be assigned, before determining the text difficulty score.

For example, some embodiments may use an algorithm, such as a probabilistic statistical classification model (e.g., a logistic regression algorithm), to determine correct weights for each of the features in the set of features identified in resources within a training corpus comprising one or more training resources. A first weighted value may be assigned during lexical feature extraction of steps S301-S309. Each of the first values assigned to the features then receive a second value determined through analysis of the features of the text. Therefore, in this exemplary embodiment, the final text difficulty score is determined using each of the first weighted values obtained during feature extraction and each of the second weighted values determined through analysis of the text.

In some embodiments, as in the present example, the textual features of a resource logically separates text of resources into various weighted scores based on a difficulty determined for each identified feature. Then, an algorithm, such as a logistic regression model, converges the weights across a plurality of resources in a corpus such that weights for the features are determined based, at least in part, on their statistical distribution across resources in the corpus.

In a next step S311, the resource is grouped with resources of similar difficulty based on the text difficulty score calculated for the text. This step may categorize resources based on text difficulty score into a leveling system corresponding to a leveling system classifying language learners' proficiency in a relevant language.

In some embodiments, resources are grouped by proficiency level based on comparable text difficulty scores. In such embodiments, after the text difficulty score is calculated, resources are grouped on a scale comprising various thresholds in a leveling system used for categorizing text difficulty of resources. For example, a first level comprising a set of corpora having text difficulty scores in the range of 'A' to 'C'; or a Level 'A' comprising a set of corpora having text difficulty scores in the range of '0.1' to '0.3' on a global scale from 0 to 1.

Some embodiments of the text difficulty calculator may implement a clustering analysis to group the various resources by difficulty levels. After assigning weights to each of the textual features of resources in a corpus, the assigned weights for the textual features of a given resource effectively separate the text of the resource into various difficulty categories according to each identified feature, then a logistic regression algorithm converges the weights to categorize the overall resource into an appropriate difficulty category. Some embodiments may implement a principal component analysis to determine an optimal number of clusters based on the variance.

In an example of the text difficulty calculator using a clustering method, the clustering method used is a k-means methodology in which the inputs are the number of clusters implemented and a combination of syntactic and semantic features computed from the resource. This methodology may also determine the optimal number of proficiency level groups, or clusters, of resources in which to categorize resources in a resource store.

In this example, the features of the text may include a proportion of words in the resource that may be found in the Academic Word List, adjective variation (AdjV), adverb variation (AdvV), bilogarithmic type to token ration (B_TTR), lexical word variation (LV), modifier variation (ModV), noun variation (NV), average number of characters (NumChar), average number of syllables (NumSyll), squared VV1 (SVV1), Uber Index (Uber), and verb variation-I (VV1).

In another example, embodiments of the text difficulty calculator module may comprise two components: (a) a program derived from sckit-learn for clustering analysis, and (b) syntactic complexity code. The text difficulty calculator may use a known scripting language, such as Python coding, to extract the set of semantic and syntactic features and a natural language tool kit for part-of-speech tagging to effectuate word-feature identification and text difficulty calculation.

Distractor Generator

Some embodiments of the system or method of language learning may include a distractor generator module. A distractor generator module is a component of a computer program product embodied on a machine-readable medium and executed by a processor to perform the specified functionality.

In some embodiments of a language learning system, distractors may be used in customized language-learning lessons for a language learner. The distractor generator module may automatically identify and generate syntactic, orthographic, phonetic, and semantic (synonym and antonym) distractors.

Those embodiments of a language learning system implementing a distractor generator may include a computing device of a language learner, which may connect to a distractor store to request distractors when a certain word is being tested. A distractor store may be a database comprising a non-transitory machine-readable storage medium storing one or more distractors generated by the distractor generator.

Embodiments of a language learning system implementing a distractor generator may include keyword store storing keywords extracted from text of resources by the language learning system. Or, in some cases, keywords may be input from a user interface of a computer device of a language learner, content curator, or other user such as an administrator.

Embodiments of a distractor generator may access one or more dictionary sources to identify a rough approximation of a definition of a word to return appropriate and effective distractors. A dictionary source may be a keyword store of the language learning system built by keywords extracted from resources stored in the resource store. A dictionary source may be another database in the system storing words in associated with a definition. A dictionary source may be an externally referenced source, such as a website or a commercial service providing searchable access to words and their associated definitions.

Embodiments of a distractor generator may use a number of different sources and tools as dictionary source. For example, a dictionary source may be a licensed dictionary software tool having definitions and, in some cases, pronunciation data. Commercially-available dictionary tools may also be dictionary sources used, such as WordNet, which is a dictionary software tool representing relationship between clusters of words. And, in some cases, the keyword store may be implemented as a dictionary source; but, embodiments of the keyword store may have metadata attached to each entry, like audio pronunciation, which may be generated through associated recorded speech. Moreover, metadata may relate distractors and keywords in the keyword store back to resources with which they are associated.

Some embodiments of a distractor generator may use a heuristic word sense disambiguation function, which may be aided by a natural language processing toolkit of a known computer scripting language, such as Python or Java. The distractor generator may then identify a similar definition in a dictionary source such as a keyword store or an external dictionary source such as an online computer-searchable Oxford Dictionary.

Exemplary embodiments of a distractor generator module may include such components as a natural language processing toolkit for part-of-speech tagging, pyEnchant, aspell, Oxford ESL Dictionary, and/or WordNet.

Figure 4:
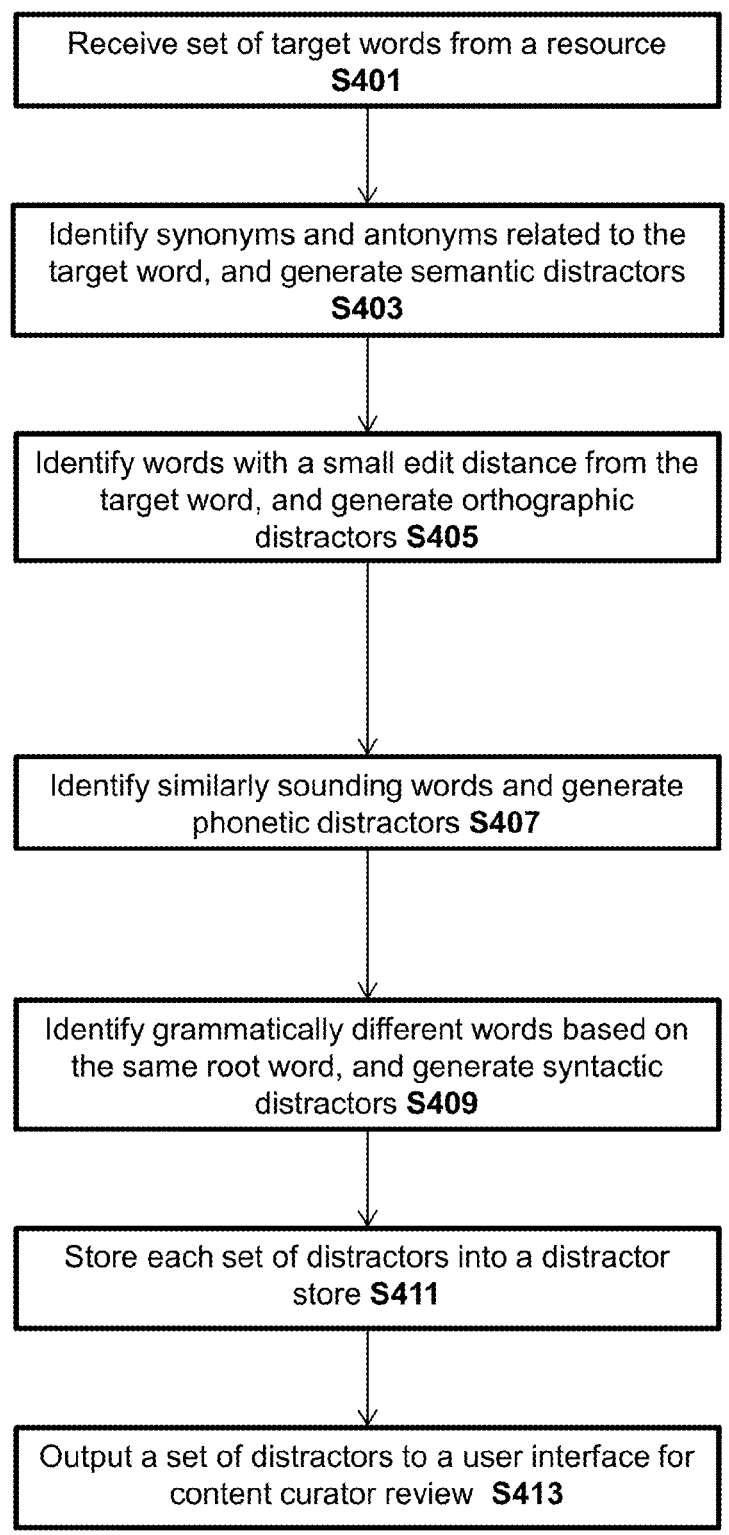
FIG. 4 shows a flowchart of an exemplary embodiment of the method executed by the distractor generator module.

FIG. 4 shows a flowchart of an exemplary embodiment of the method executed by the distractor generator module.

Embodiments of a distractor generator module may automatically identify and generate different types of distractors for a target word. In some embodiments of a language learning system, the distractors generated by a distractor generator may be implemented in for various pedagogical purposes in language learning, such as evaluations and/or educational activities.

In a step S401, a distractor generator receives a target word from a module or component within a system, which may be a language learning system. A distractor generator may receive a single target word or a plurality of target words, for which distractors will be automatically generated.

In some embodiments of a language learning system, a distractor generator may receive a set of keywords extracted from a resource. The set of keywords comprising one or more target words for which distractors may be automatically generated. The distractor generator may automatically generate a set of distractors for each of the target words.

In a step S402, the distractor generator module generates a set of semantic distractors related to the target word. The set of semantic distractors may comprise one or more synonyms of the target word. Additionally or alternatively, the set of semantic distractors may comprise one or more antonyms of the target word.

Embodiments of a distractor generator may use natural language processing, implemented by, for example, a natural language processing toolkit of a known computer scripting language, to associate similar words and/or definitions from a dictionary with the target word, to aid language learners to better master the target word.

A distractor generator may search dictionary sources to identify one or more synonyms of the target word and one or more antonyms of the target word. A dictionary source may be a keyword store, another dictionary service within the language learning system (e.g., a manually updated text file), and/or a dictionary computer service external to the system (e.g., the Merriam-Webster's® website). The distractor generator may generate a set of semantic distractors by choosing one or more of the identified synonyms and/or one or more of the antonyms. The set of semantic distractors may be words to aid language learners as they master what the target word means. Some embodiments of the language learning system may implement the semantic distractors to distract language learners from the correct meaning of the target word. The distractor generator may automatically generate the set of semantic distractors to aid language learners understand a definition of the target word.

In a next step S405, a distractor generator may identify a set of orthographic distractors for the target word. Orthographic distractors may be words having a small edit distance with respect to a target word. An edit distance is the total number of letter-insertions and/or letter-deletions required to have one word resemble a second word. For example, changing the word "could" to "cold" is an edit distance of 1 because only a letter deletion was required to change "could" to "cold." Likewise, in another example, changing "could" to "would" is an edit distance of 2 because one letter is deleted and one letter is inserted. And, in another example, changing "could" to "should" is an edit distance of 3 because one letter is deleted and two letters are inserted.

Using words found in one or more dictionary sources, the distractor generator in step S405 may locate words having a minimal edit distance in relation to a target word that is going to be exercised. That is, the distractor generator may identify an edit distance from the target word to each of the words in a dictionary source. The distractor generator may rank the words of a dictionary according to smallest edit distance. A distractor generator may then start from a word that is ranked with smallest edit distance and then walk through the ranked words towards word having larger edit distances until the set of orthographic distractors is generated. The set of orthographic distractors comprises words having small, or the smallest, edit distances satisfying a difficulty level related to the abilities of the learner.

The smaller the edit distance is between two words, the harder it may be for a non-native speaker to distinguish the two words from each other. In contrast, words having a larger edit distance may be easier to distinguish. Applying this to generating orthographic distractors, smaller edit distances between orthographic distractors and a target word may result in comparatively more difficult distractors for language learners. The difficulty level of orthographic distractors may therefore be adaptably varied by selecting words from the dictionary source having larger/smaller edit distances.

In some embodiments, selecting words having the smallest desired edit distance may be based on a pre-determined amount of words to be used. For example, if there are to be 10 comparatively difficult orthographic distractors in the set, then 10 words ranked as being closest to the target word are selected.

As described above, in some embodiments, a minimum edit distance, a maximum edit distance, or an exact edit distance, may be used to selected words in the set of orthographic distractors based on a desired difficulty level. The set of orthographic distractors may be determined by a difficulty setting, which may allow the distractor generator to automatically adapt complexity of orthographic distractors selected and the amount of orthographic distractors in the set. For example, an exact edit distance of 3 may be used to generate a comparatively less difficult set of orthographic distractors. In this case, all of the words identified as having an edit distance of 3 in a dictionary may be included in the set of orthographic distractors. The number of orthographic distractors may be limited by various means previously described, or may include all of the words satisfying the edit distance criteria.

It is to be appreciated that other algorithms for selecting orthographic distractors based on an edit distance in relation to a target word may be used to generate a set of orthographic distractors. An ordinary artisan would appreciate that other algorithms to automatically identify and generate orthographic distractors based on edit distance may fall within the scope of one or more portions of the invention described herein.

In a next step S407, a distractor generator may generate a set of phonetic distractors related to a target word. A phonetic distractor may be a word tending to cause distraction based on the phonetic similarity between words. Embodiments of the distractor generator may automatically identify one or more phonetic distractors in one or more dictionary sources and then generate the set of phonetic distractors from one or more of those identified.

Phonetic distractors may be words that sound similar to a target word but are not intended to be identically pronounced when spoken. A phonetic distractor may be a word that sounds similar to the target word, but may also have a small edit distance in relation to the target word. Some embodiments of the language learning system may utilize the set of phonetic distractors in pedagogical learning activities where, for example, language learners must choose between two different items that sound similar to one another.

Some embodiments of a distractor generator may comprise a step S408 in which words that sound identical, or homophones, are excluded from the set of phonetic distractors. In such embodiments, a distractor generator may recognize a word as being a homophone of a target word. For example, in some cases, a homophone may be included to a set of orthographic distractors because the homophone has an edit distance meeting the criteria for orthographic distractors; meaning the homophone could be included in the set of phonetic distractors. But embodiments implementing a step S408, or the like, may identify homophones and exclude them from the set of phonetic distractors.

In a next step S409, a distractor generator may identify a set of syntactic distractors. A syntactic distractor may be a word related to a target word but differs in some grammatical fashion, e.g., the word is a different conjugation of a verb, the word is a verb that agrees with a different person being referenced (first-person, second-person, third-person), the word is a noun form of a verb, or the word is a verb form of a noun.

In a next step S411, a distractor generator may store each of the sets of distractors into a distractor store. In some circumstances, step S411 may automatically update an existing set of distractors or receive an input from a user interface of a content curator's computing device changing one or more of the distractors.

In a next step S413, a distractor generator may output one or more of the automatically generated sets of distractors to a user interface of a computing device.

In some embodiments, the user interface receiving the output of the distractor generator may be that of a content curator who may review automatically generated distractors for accuracy and consistency. Should the content curator wish to amend a set of distractors, such embodiments may provide for the content curator to make necessary changes via the user interface.

In some embodiments, the user interface receiving the outputted distractors may be that of a language learner who may review automatically generated distractors for accuracy and consistency; particularly where the learner was the originator of the resource from which words was extracted. Should the learner wish to amend a set of distractors, such embodiments may provide for the learner to make necessary changes via the user interface.

In some embodiments, distractors or sets of distractors may be associated with keywords through relational metadata. That is, distractors may be stored in a distractor store with metadata that associates keywords to particular distractors. Similarly, in some embodiments of a keyword store, as described herein, keywords may be stored with metadata the associates distractors with particular keywords.

Learning Activities and Activity Sequences

Embodiments of a language learning system may include a learning module lessons in which the objective is having a language learner demonstrate knowledge of a concept or helping a learner learn a concept by performing specific learning activities.

A learning module may generate a learning activities of various types that are designed to foster various language skills such as reading, writing, listening, and speaking proficiency. The various activity types may also focus on vocabulary building, grammatical proficiency, and/or pronunciation, among other skills. Examples of activities may include a multiple choice question activity, a vocabulary matching activity, a speaking focused activity, a pronunciation focused activity, a writing focused activity, a grammar focused activity, a listening focused activity, a reading focused activity, a spelling focused activity, identifying a vocabulary word activity, an understanding of audio information activity, an understanding of video information activity, and a reading comprehension activity.

A learning module may dynamically generate a lesson that may comprise a number of learning activities tailored for language learners. When dynamically generating a learning activity, the language module may utilize output generated by a keyword extractor, a distractor generator, and/or a text difficulty calculator.

In some embodiments, learning activities may be customized based on user data associated with learners that is stored in a user data store. For example, learning activities may be varied by difficulty to correspond to a language learner's proficiency level. Other variations based on user data may include customizations based on a language learner's personal goals, needs, and performance. The learning module may automatically utilize output from various modules and data stored in databases to, in turn, automatically generate learning activities suited for a language learner.

The system may set forth a pedagogic path for each level of language learning, whereby each pedagogic path comprises a series of learning activities. The learning activities can vary based upon the learner's needs and proficiency level, as well as different constraints, such as a number of words used in an activity, a time constraint, whether to use audio or textual hints (e.g., revealing part of a word). The system can dynamically build an appropriately difficult activity based upon the type of learning activity required by the learner's past performance.

An exemplary activity for a learning activity may be a vocabulary activity in which the learner identifies synonyms of a given word. The synonyms used in the learning activity may be chosen based upon the needs and proficiency of the learner. The learning activity types are established within the system, but the content and words are dynamically adjusted for each learner and allow for a customized activity.

Each learning activity may use distractors. The system chooses appropriate distractors based on their type and relationship to the target word for use in different activities, including multiple choice questions, matching activities, spelling activities, activities for reconstructing a text, and memory games. The learning activity module may score a learner's performance and automatically assign a grade to the learner for one or more skills in an activity.

At a higher performance grouping level, more difficult distractors may be used. Learning activities may be automatically adapted within a lesson, or for a next lesson, in response to a change in the learner's skills and/or overall proficiency. In some embodiments, the learning activity module may update the learner's profile in the user profile store to reflect grades and changes in the learner's abilities.

For example, a lower-level learner might have to complete a blank space with a correct word and be presented with options such as the target word, an antonym, and another word with a similar spelling. A higher-level learner performing the same activity might have increasingly difficult options such as more distractors and/or more similarly spelled words.

A lesson may comprise a series of learning activities that may be derived from the combinations and permutations corpora, keywords, and distractors. Each lesson relies on resources, such as a document, and includes a specific series of learning activities that may increase in difficulty. For example, an activity sequence focused on reading and spelling would begin with an initial reading comprehension activity, then move to a vocabulary acquisition activity, and finish with one or two spelling activities. As the learner demonstrates proficiency and improved performance, the keywords targeted can get increasingly difficult.

The difficulty level of a given learning activity may be determined by a difficulty level (which is chosen based on a user's proficiency, i.e., performance on assessment) and learning activity difficulty level (which is chosen based on a user's performance within lessons/courses). The learning activity difficulty level may be related to the text difficulty level of the underlying resource used in the learning activity. The text difficultly level may be determined with an algorithms using metrics such as a readability index, average sentence length, number of words from Oxford 3 k, number of words from the AWL, number of subordinate clauses, number of relative clauses, number of common simple tenses, number of common progressive tenses, number of common future tenses, or words tagged in an image.

For example, a relatively high text difficulty score for a resource may indicate more difficult or complicated language in the text because text contains words that appear less frequently, longer sentences, academic words, and high relative frequency of complex forms.

A relatively high learner proficiency score indicates that a learner is very proficient in one or more language skill domains, such as reading, writing, listening, and speaking. In other words, a learner with a high proficiency score is said to have high ability scores in various specific language skills. Learners having a relatively high learner proficiency score may be able to handle resources, and content in resources, having more difficult language, indicating that such learners have a robust vocabulary, a strong command of grammar, and strong performance across language skill domains, i.e., high abilities in specific language skills. Resource difficulty levels, such as a text difficulty score, may be mapped to learner proficiency levels so that all resources and learning activities that learners presented with generally contain language at a level of difficulty that is at, or sometimes slightly above, a learner's current level.

Embodiments of a learning activity module may implement various multimedia sources, including audio input or output, video input or output, textual input or output, and image input or output. A learner's responses to a learning activity may be saved in a user data store for assessing the user's performance and/or for feedback from a tutor or content curator. In some learning activities, a learner may receive a resource having errors in the text, and be required to edit it themselves. The learner may then submit this completed learning activity for asynchronous offline feedback.

Learning activities and each type of learning activity may be modified to be more or less difficult while holding the underlying resource constant. Learning activity difficulty may be influenced by, for example, the difficulty of distractors that are used. For example, an "easy" version of a learning activity would use "easier" distractors than the "difficult" version. Other non-limiting examples of how the difficulty of learning activities may be varied may include adjusting the number of items tested, the presence/absence of a timer, and/or other activity-specific variations such as longer words in a type of activity that is vocabulary focused. In some embodiments, learning activity difficulty may be manually modified or automatically adapted for learners within their coursework tracks and lessons.

Adjusting difficulty may also be based on a word difficulty. Words may have difficulty scores associated with them. In some cases, words may be normalized on a zero to one scale so that they may be associated with learning activities appropriately. Inputs into word difficulty scoring may include frequency within a variety of corpora, such as the American National Corpus, as well as metrics such as number of syllables and number of definitions for the word. Word difficulty levels may be used to sequence learners' exposure to words within a lesson/learning activity sequence. Learners' word mastery scores may be used to determine which words to feature in various learning activities.

Examples of the Graphical User Interface for a Learner

Figure 5:
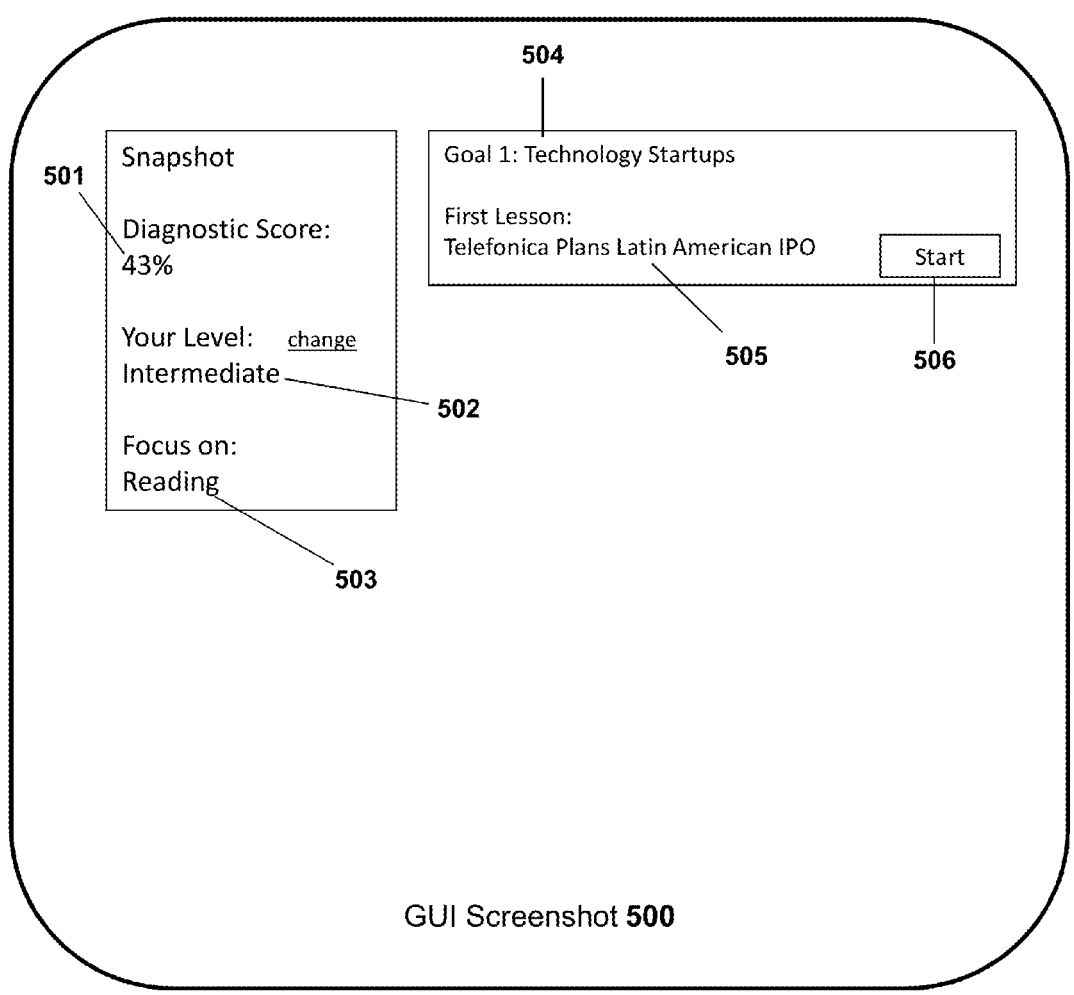
FIG. 5 shows a screenshot of an exemplary embodiment of a graphical user interface presented to a learner to begin a language-learning lesson.

FIG. 5 shows a screenshot of an exemplary embodiment of a graphical user interface (GUI) 500 displaying a home menu before a lesson 505, to a language learner, on a monitor of the learner's computing device. The GUI screenshot 500 comprising a diagnostic score 501, a language proficiency level of the user 502, a learning focus 503 on a particular language skill, a goal 504 for the coursework, a lesson 505, and a start button 506. The screenshots 600, 700, 800 are examples learning activities of various activity types, which were dynamically generated for the learner; together they may comprise a lesson 505.

Figure 6:
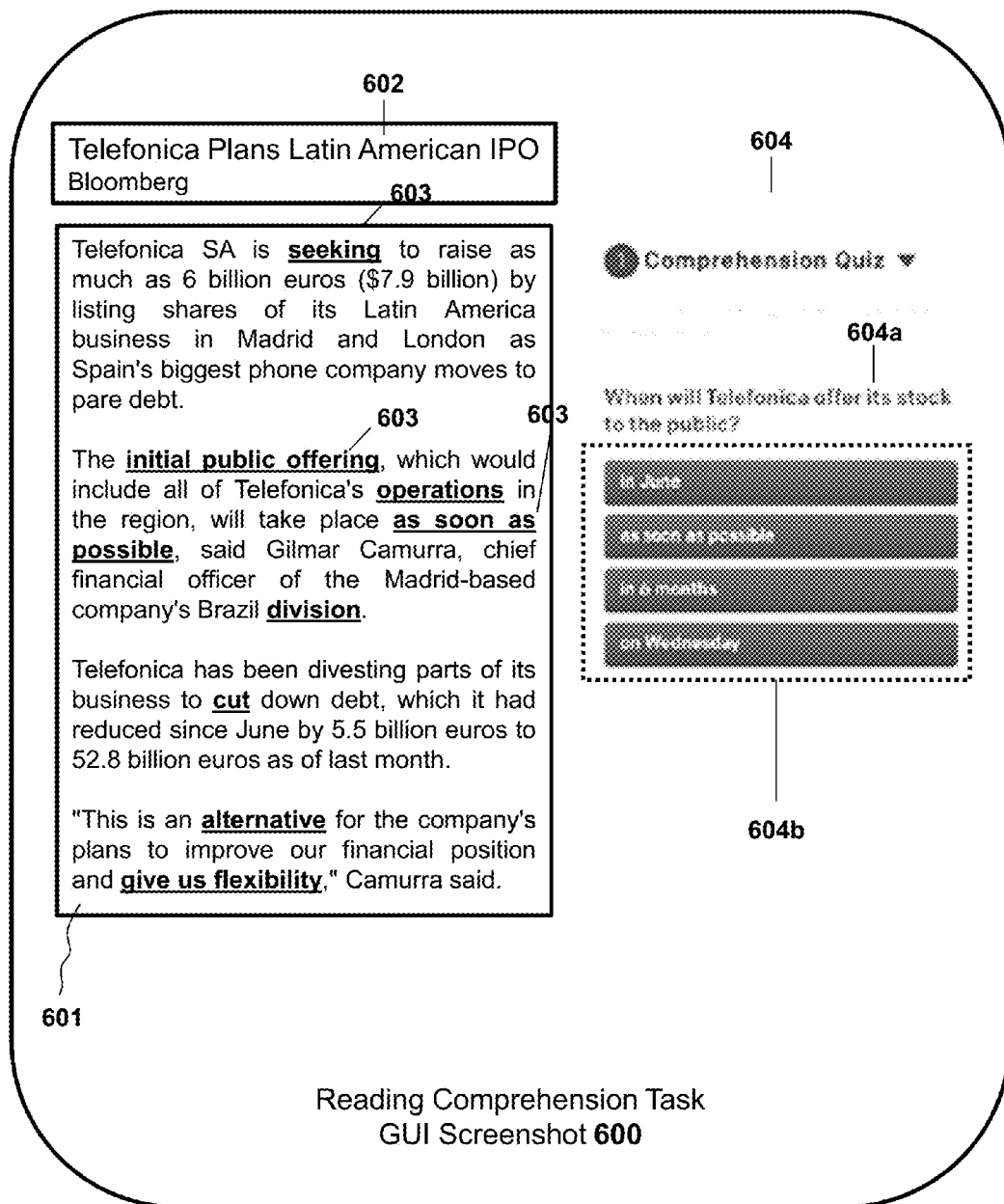
FIG. 6 shows a screenshot of an exemplary embodiment of a graphical user interface for a learner to engage a reading comprehension activity.
Figure 7:
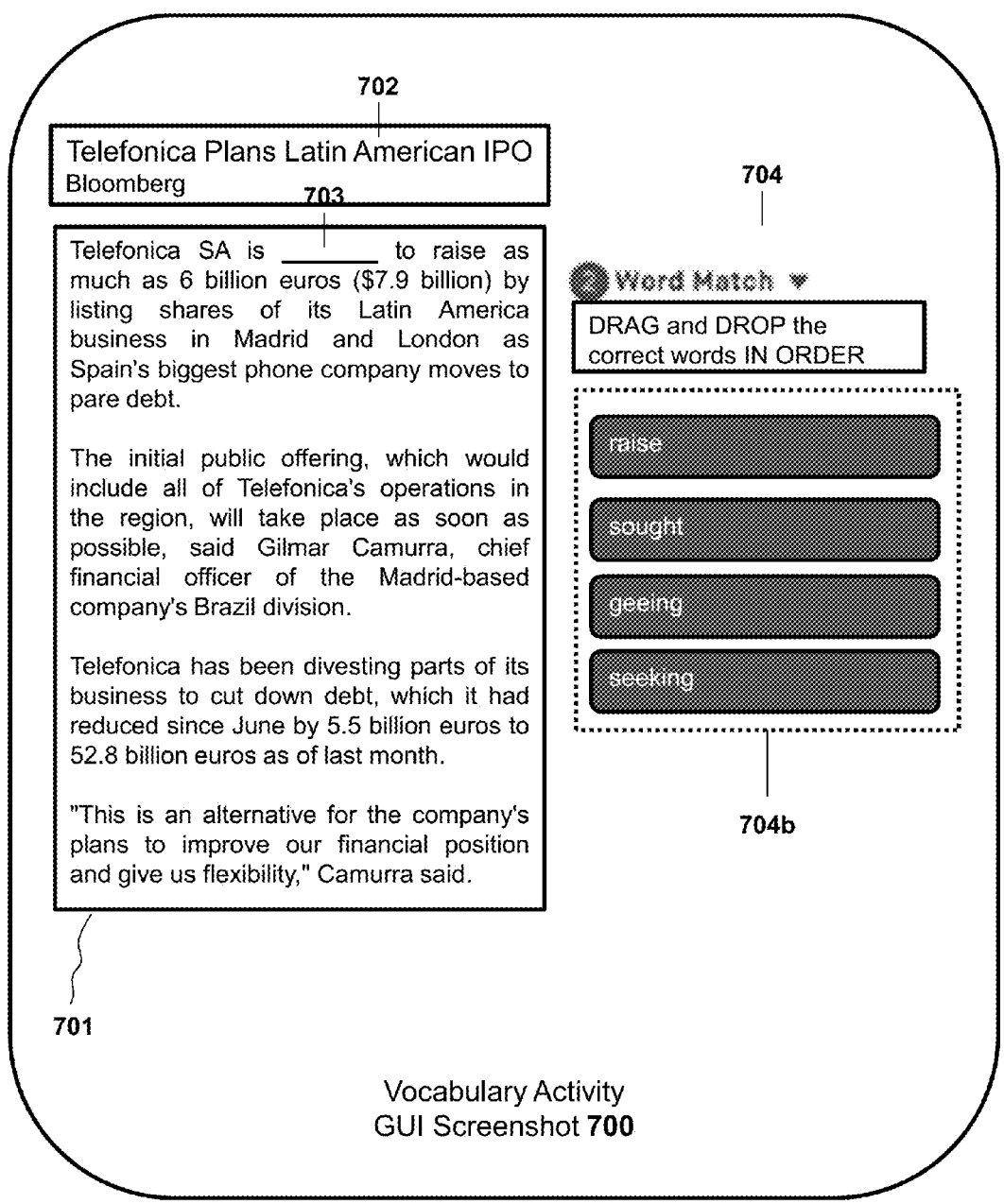
FIG. 7 shows a screenshot of an exemplary embodiment of a graphical user interface for a learner to engage a vocabulary activity.

An activity in this exemplary lesson 505 may be reading comprehension, as shown in FIG. 6. Another activity in this exemplary lesson 505 may be a vocabulary activity, as shown in FIG. 7. Another activity in this exemplary lesson 505 may be an activity involving spelling with different subset of keywords, as shown in FIG. 8.

FIG. 6 is a screenshot of a GUI 600 for a learner to engage in a reading comprehension activity prepared by the language learning system. The exemplary GUI screenshot 600 for a reading comprehension activity may comprise text 601 of a document resource that is used for the exemplary lesson 505, a document title 602, one or more highlighted keywords 603, and a reading comprehension quiz 604 comprising a question 604*a* and a set of multiple choice answers 604*b*. The exemplary screenshot of a GUI 600 may highlight various keywords 603 and presents a comprehension quiz 604 that implements the keywords 603 and a set of distractors in the form of multiple choice answers 604*b*.

FIG. 7 is a screenshot of a GUI 700 for a user to engage a vocabulary activity prepared by the language learning system. The exemplary GUI screenshot 700 for a vocabulary activity may comprise text 701 of a document resource, a document title 702, a redacted word 703 in the text 701, and a word match question 704. The word match question 704 having a set of multiple choice answers 704*b* in which the correct answer corresponds to the redacted word 703.

Figure 8:
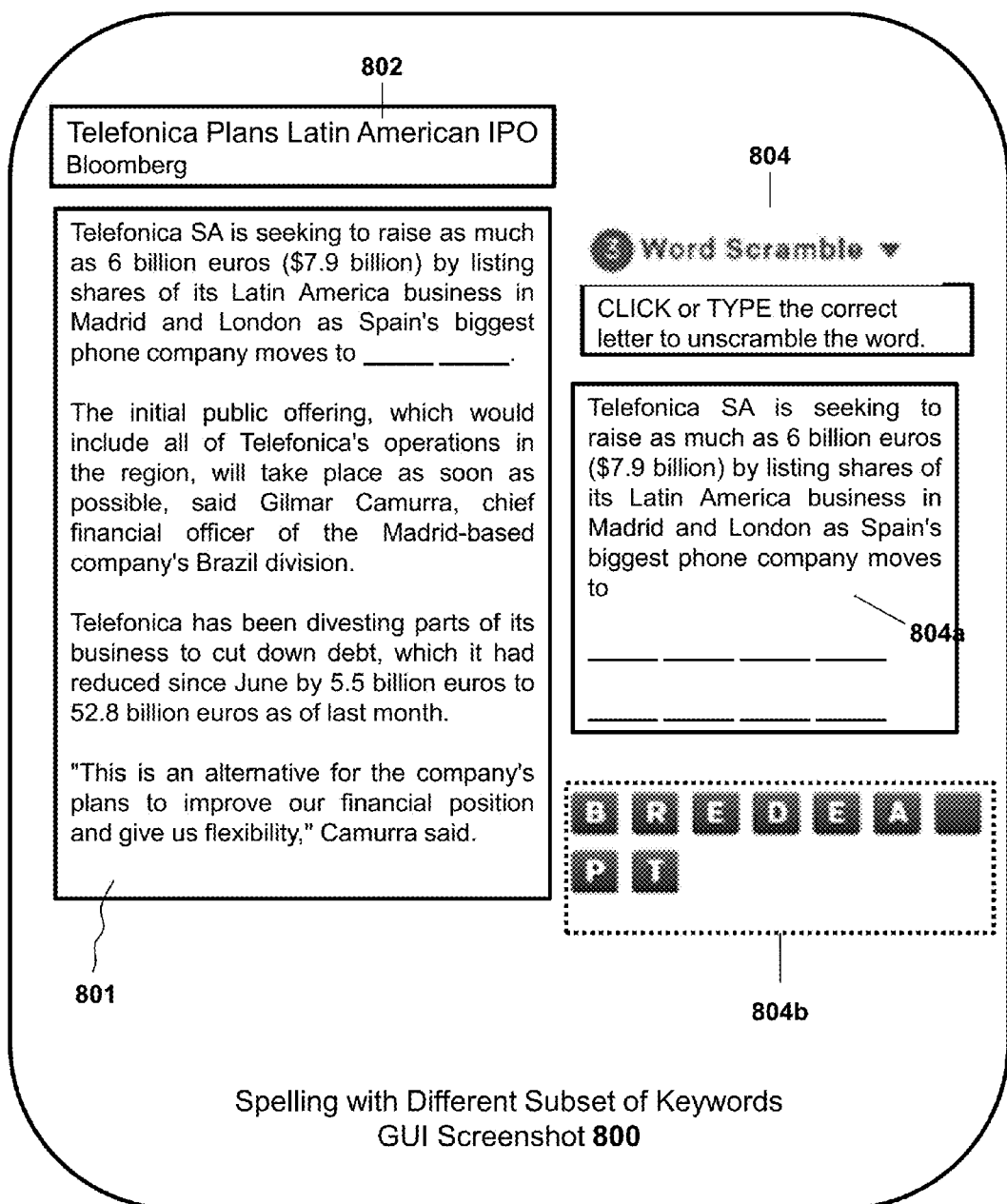
FIG. 8 shows a screenshot of an exemplary embodiment of a graphical user interface for a learner to engage a spelling activity.

FIG. 8 is a screenshot of a GUI 800 for a user to engage a spelling activity prepared by the language learning system. The exemplary GUI screenshot 800 may present an activity involving spelling with different subset of keywords. The GUI screenshot 800 comprising text 801 of a document resource, a document title 802, a redacted word 803 in the text 801, and a word scramble quiz 804 comprising a question prompt 804*a* and a scrambled set of letters 804*b*.

Example of a Learning Activity Module

Figure 9:
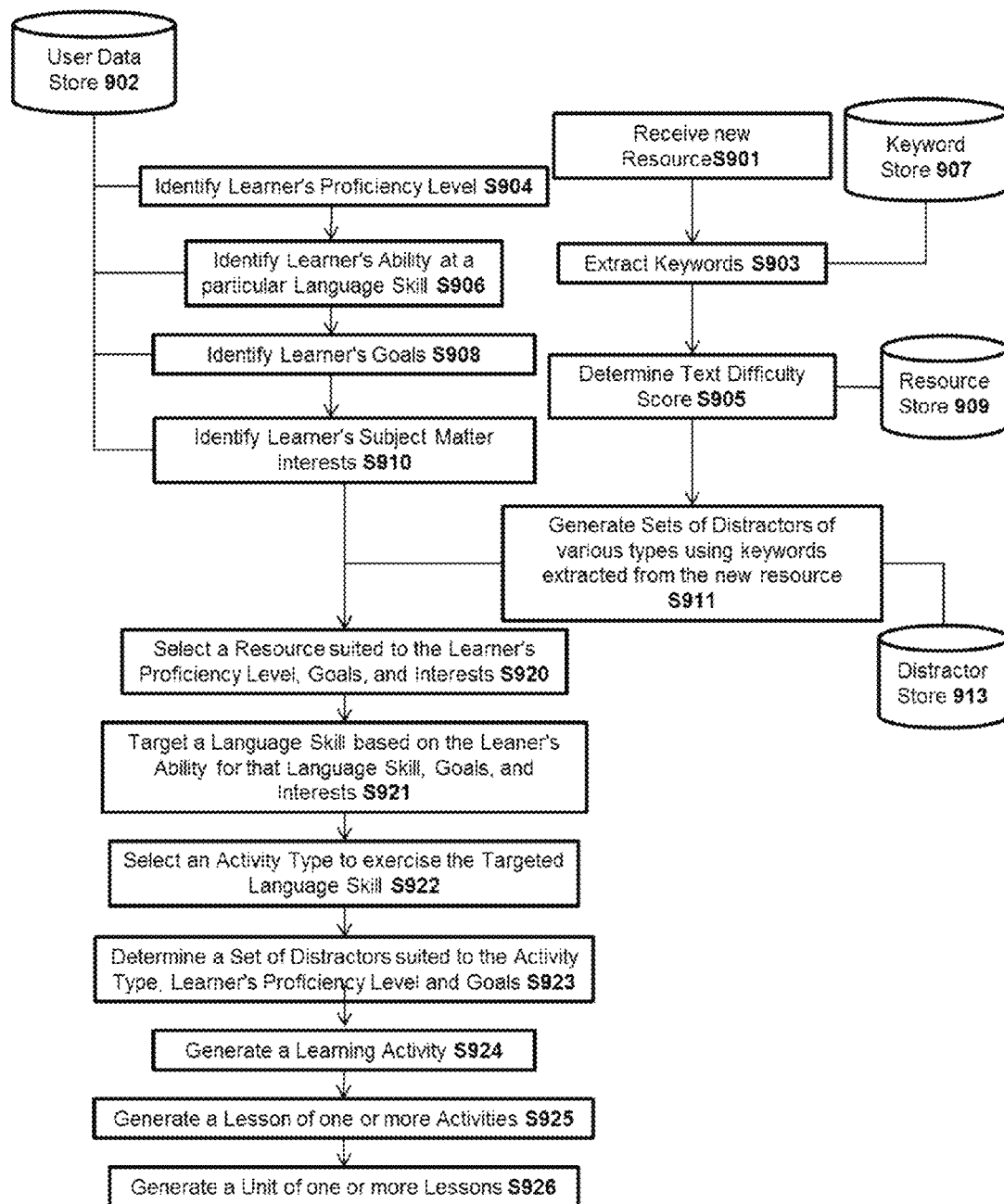
FIG. 9 shows an exemplary method embodiment of a language system implementing a learning module.

FIG. 9 shows a method of a language system implementing a learning module according to an exemplary embodiment.

The exemplary method embodiment of FIG. 9 comprises steps S901, S905, S911, S904, S906, S908, S910, S920, S921, S922, S923, S924, S925, and S926, and may implement a user data store 902, a keyword store 907, a resource store 909, and a distractor store 913.

In a first step S901, a language learning system may receive a new document resources comprising text. The new text may be received from a computing device of a language learner ("learner"). The new text may be input from a computing device of a content curator. The new text may be automatically downloaded or transmitted from a text-producing source, such as, for example, a website, a blog, a news outlet, or a textbook publisher.

In a step S903, a keyword extractor module implemented by the system may extract one or more keywords from the new text. The keywords may be extracted according to an algorithm adapted to identify and extract keywords that are pedagogically valuable words effectuating language learning. The keyword extractor module may be adapted to determine a word difficulty score for a keyword. The keyword extractor module may be adapted to associate one or more other attributes to a keyword, such as word length, number of syllables, and/or a part-of-speech.

A keyword extractor module may store the extracted keywords in a keyword store 907, which is non-transitory machine-readable storage medium storing keywords. A keyword store 907 may store data associated with the keywords, such as word attributes, a word difficulty score, source document, and/or keys associated with the keywords stored in the keyword store 907.

In some embodiments, the keyword extractor module may extract and store different keywords depending upon a profile of the learner. Keywords may be assigned a more difficult keyword score if they, for example, are associated with an esoteric or unique definition. Keywords may also be more difficult if they have are longer by number of letters and syllables. Keywords may be more difficult if they have silent letters, abnormal pronunciations, or non-intuitive spellings. In such embodiments, a keyword extractor may generate an additional word score (aside from the word scoring done to determine candidate keywords) to rank words in terms of likelihood of difficulty for non-native speakers using word length and word and part-of-speech frequency in external corpora. As discussed below, a learning activity may be made more difficult by using distractors that are intended to test more difficult keywords extracted from a text.

In a next step S905, a text difficulty calculator module may determine a text difficulty score for the text of a new resource. In the exemplary embodiment, a new document resource comprising text is received, the text difficulty score is determined, and then the new resource may be stored into a resource store 909. The resource store 909 may be a non-transitory machine-readable storage medium storing one or more resources. In some embodiments, the resource store 909 may also store metadata associated with resources that describe various attributes of the associated resources, such as a text difficulty score. In some embodiments, a document may already be stored in the resource store 909, in which case step S905 would not be necessary.

In a step S911, a distractor generator may generate a set of one or more distractors. Distractors may be generated and stored into a distractor store 913. Distractors may be of various different types, each of the types are designed to exercise language learners' abilities in particular language skills, i.e., spelling, vocabulary, phonetic distinctions.

In some embodiments, the distractor generator may generate as many distractors as needed to test each of the extract keywords. Distractors may be of varying difficulty based on a number attributes of a distractor, such as, for example, the difficulty of the underlying keyword being testing, or the closeness of the keyword and distractor.

Some embodiments of a learning module may utilize a user data store 902, which a non-transitory machine-readable storage medium that stores user profiles associated with language learners. The user profiles may comprise information about language learners, such as a learner goal for the learning the language, a subject matter interest for content contained within text, ability scores for language skills, and/or the learner's overall proficiency level at the language.

In a step S904, a learning module may identify a learner proficiency level in the user data store 902. The proficiency level may be an overall valuation of the learner's skill level, whereas an ability may be for a particular skill. A proficiency level may be determined by amalgamation of assessments individual abilities, or may be determined by known means of assessing a language proficiency level.

In a step S906, a learning module may identify the need for targeted language skill practice based on the scored abilities of the learner in the user data store 902. An example of a language skill may be reading comprehension or spelling. An ability score may be an indicator of the learner's ability to perform that particular language skill. The learning module may make use of any number of language skills when preparing learning activities. A learner profile may store an ability score for each of the language skills exercised by the learning module.

In a step S908, a learning module may identify one or more goals that the learner has for learning the language. A goal may be, for example, studying for the TOFEL examination, preparing for a tourism vacation, preparing for a business trip, school course, professional requirement or military deployment. A learner may be associated with more than one goal. A goal may be a pre-determined list from which the learner may select, or a goal may be input from the learner at a prompt. A goal may also be input by a content curator or other administrator.

A learning module may prepare learning activities relative to a learner based on the learner's needs, i.e., weaker abilities in specific skills. And, in some embodiments, the learning module may prepare lessons so that learners may achieve certain goals. That is, the learning module may track learners' progress of their proficiency level and abilities in specific skills relative to their stated goals. A goal may be met when a learner's proficiency level and/or abilities reach a level comparable to their goal. Learners having a goal demanding a higher proficiency level, such as preparing for the TOEFL, may receive a longer set of lesson and/or a more comprehensive set of lessons, as compared to learners who have a less demanding goal, such as learning basic vocabulary for casual conversation.

For example, two learners, who are at the exact same proficiency level, may have different goals in which they wish to attain. The first learner, for example, may only want to be able to order coffee in the new language, in which case the first learner would be able to reach that goal more quickly and the content the first learner would interact with would generally relate to ordering food and drink. If a second learner, at the same proficiency level, wanted to become fluent in the new language, then the second learner would have a longer collection of coursework (e.g., longer lessons, and/or more lessons). In this example, both the first learner and the second learner might begin with learning activities directed towards ordering coffee or ordering food and drink, because those were learning objectives that both learners wanted to be able to accomplish. The second learner, however, would then interact with learning activities involving increasingly difficult language skills. In cases, the second learner would receive longer lessons comprising more learning activities as compared to the first learner.

Some embodiments of the learning module may allow learners to take an achievement test to determine whether learners have met their stated goal. Learners' proficiency levels and abilities may be scored and tracked throughout their interaction by the language learning system. In some cases, the learning module may inform users when they reach a proficiency level comparable to their stated goals. Learners may take an achievement test that assesses whether learners have achieved their goals.

In a next step S910, a learning module may identify a learner's content interest of the subject matter of potential resources, according to the learner's interests stored in the user data store 902. A learner's interest may be, for example, a sport. These may be input from a user interface of the learner in which the learner lists interests.

In next steps S920-S926, a learning module selects a resource to utilize for generating a series of learning activities, where the series of learning activities may be a lesson. The lesson may be a set of learning activities generated using the identified learner attributes from steps S904, S906, S908, and S910, and also using the learning activity building blocks generated in steps S901, S903, S905, and S911.

In a next step S920, a resource may be selected from the resource store based on one or more learner attributes. A resource may be selected according to any permutation of learner attributes, such as a learner's proficiency level, goals, and interests.

In some embodiments of the learning module, learning activities may be generated to automatically include a resource containing content that is relevant to the learner's interests. For a document resource, the content of the text may be identified using metadata associated with extracted keywords. The content of the text may also be identified by some other known natural language processing technique that may identify and/or categorize subject matter of a resource, a corpus, or other collection of resources.

As an example of delivering certain resources based on their content, a learner with an interest in soccer may interact with learning activities related to resources describing a recent soccer match, text explaining the rules of soccer, or text detailing the history of a famous soccer club.

As previously mentioned, some embodiments of a learning module may select resources based on how complicated their content is. That is, in some cases, resources' difficulty scores may be based, in part, on how complicated their content is. For example, if a novice learner is a physicist with an interest in complicated scientific topics, then text whose content discusses the complicated scientific topics in the language being learned, may be too difficult to effectively teach the new language to the novice learner. Thus, some embodiments of a learning activity module may use a text difficulty score to determine an appropriate resource to fetch from a the resource store when building a learning activity.

Embodiments of the learning activity module may vary permutations of learners' attributes and permutations of learning activities' building blocks are used when generating learning activities.

In a next step S921, a learning activity module may target a particular language skill to exercise in the learning activity being generated. The particular skill being targeted is based on the learner's abilities in individual language skills. A learning activity module may adaptably construct a series of learning activities that employ activities addressing weaknesses in the particular skills of the learner.

Embodiments of a learning activity module may also adaptably construct learning activities based upon the goals of the learner. For example, if the learner is a tourist, then learning activities may comprise activities focusing on simpler vocabulary about landmarks or directions. In a contrasting example, a learner studying for the TOEFL may receive more difficult grammatical activities.

Next, in a step S922, by targeting a particular language skill in step S921, the learning activity module may determine which type of activity the learning activity must employ to appropriately address the particular language skill. For example, when a learning activity module determines that a learner must target phonetic understanding skills, the learning activity module may automatically generate a phonetics-based activity.

Non-limiting examples of activities may include: a reading comprehension activity (e.g., a multiple choice question about the content of a corpus or resource just consumed), a word match activity (e.g., fill in the blanks in an article choosing from list of all available keywords), a vocabulary challenge (e.g., show a definition and answer multiple choice questions to identify the target keyword, in text or with audio), a sound drop activity (e.g., in a range of text, have missing words and ask user to listen to multiple audio files to find the match and drop it in) a memory game activity (e.g., have cards with keywords and synonyms/definitions covering the original content and flip them over concentration style to match the words), and a word scramble activity (e.g., see a word/phrase blanked out in a range of text and have the letters re-arranged so it has to be spelled out by clicking on them in order).

In a next step S923, a learning activity module may select a set of distractors, derived from the selected resource, which are suited to a type of learning activity.

A learning activity module may identify and select distractors appropriate for the type of learning activity determined for the learning activity within step S922. For example, phonetic distractors may be selected when the activity type will be a sound drop activity.

A learning activity module may identify and select distractors having a difficulty level that is comparable to a learner's ability in a particular language skill that is going to be exercised in the learning activity.

In a next step S924, a learning activity module may generate a learning activity using building block components of a learning activity and based on learner attributes.

Building block components of a learning activity may be a resource, a set of keywords associated with the resource, an activity exercising particular language skill, and a set of distractors derived from a dictionary source using a text's keywords (e.g., synonym semantic distractors or phonetic distractors). Learner attributes may be information describing a learner's preferences and/or information describing the learner's capabilities (e.g., an ability for vocabulary, or an overall proficiency level).

In a next step S925, a learning activity module may generate a lesson comprising a set of learning activities. The lesson, as well as the individual learning activities may be customized for a learner. A lesson may provide learners a path toward accomplishing learning goals. A learner profile may store milestones related to that path. A lesson may sequence learning activities to maximize a pedagogical value.

In a next step S926, a learning activity module may generate a unit of coursework comprising of one or more lessons. A unit may be a path for accomplishing learning goals. Lessons may be sequenced to maximize pedagogical value. Content of resources and learning activities may be personalized and customized throughout a unit.

In some embodiments, a learner may have one primary active course, composed of goal-oriented tracks, and made up of language skill-focused lessons using interest-focused resources. Units may allow users to attain a badge by passing optional achievement tests.

A learning activity module may also include synchronous or live tutoring. A learning activity module may also include asynchronous tutor feedback. Asynchronous feedback may be incorporated as learning activities in lessons that are tailored to a learner's needs. Live tutoring may be instituted in sessions that may be scheduled in conjunction with a learner's lesson or in sessions independent of a lesson, which may occur at set intervals.

Unless specifically stated otherwise as apparent from the following discussion, it is appreciated that throughout the description, discussions utilizing terms such as "creating," "providing," "calculating," "processing," "computing," "transmitting," "receiving," "determining," "displaying," "identifying," "presenting," "establishing," or the like, can refer to the action and processes of a data processing system, or similar electronic device, that manipulates and transforms data represented as physical (electronic) quantities within the system's registers or memories into other data similarly represented as physical quantities within the system's memories or registers or other such information storage, transmission or display devices. The system can be installed on a mobile device.

The exemplary embodiments can relate to an apparatus for performing one or more of the functions described herein. This apparatus may be specially constructed for the required purposes, or it may comprise a general purpose computer selectively activated or reconfigured by a computer program stored in the computer. Such a computer program may be stored in a machine (e.g. computer) readable storage medium, such as, but not limited to, any type of disk including floppy disks, optical disks, CD-ROMs and magnetic-optical disks, read only memories (ROMs), random access memories (RAMs), erasable programmable ROMs (EPROMs), electrically erasable programmable ROMs (EEPROMs), magnetic or optical cards, or any type of media suitable for storing electronic instructions, and each coupled to a bus.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A computer-implemented method comprising:
   extracting, by a computer, text from one or more resources of a corpus stored in a database, the corpus comprising a plurality of resources, each resource containing text;
   identifying, by the computer, a set of lexical features in the text of a resource of the corpus according to a lexical feature bank file indicating one or more semantic features and one or more syntactic features, wherein the set of lexical features comprises at least one semantic feature in the bank file and at least one syntactic feature in the bank file;
   storing, by the computer, into a database configured to store the corpus comprising the plurality of resources and metadata associated with each resource, metadata containing a first value associated with each of the lexical features in the set of lexical features according to the bank file, wherein the bank file indicates each value associated with each respective lexical feature;
   determining, by the computer, a text difficulty score for the text using each of the first values associated with each of the features in the set of lexical features;
   storing, by the computer, into the database storing the plurality of resources, metadata containing the text difficulty score associated with the text of each resource; and
   generating, by the computer, a portion of one or more lessons associated with a learner profile using the text of a resource selected from the database based upon metadata indicating one or more skill scores of the learner profile stored in a profile database and the metadata containing the text difficulty score of each of the resources of the corpus in the database;
   wherein the resource contains an audio track, and wherein the text is a transcript of the audio track.

2. The method according to claim 1, wherein the resource is one or more portions of a document resource containing the text.

3. The method according to claim 1, further comprising outputting, by the computer, the text difficulty score to a user interface of a computing device of a content curator.

4. The method according to claim 3, further comprising transmitting, by the computer, a set of values comprising the first values of each feature in the set of lexical features to the computing device of the content curator for the content curator to review.

5. The method according to claim 4, further comprising updating, by the computer, the text difficulty score of the text according to a score adjustment received from the user interface of the content curator.

6. The method according to claim 5, further comprising updating, by the computer, the set of values based on one or more amendments received from the user interface of the content curator.

7. The method according to claim 1, further comprising:
   comparing, by the computer, the text difficulty score associated with the resource against one or more stored text difficulty scores associated with one or more resources stored in the resource store; and
   determining, by the computer, a skill level associated with the resource according to the text difficulty score associated with the resource relative to the one or more stored text difficulty scores.

8. A computer-implemented method comprising:
   extracting, by a computer, text from one or more resources of a corpus stored in a database, the corpus comprising a plurality of resources, each resource containing text;
   parsing, by the computer, the text into one or more portions of text, wherein each portion of text is compared against a lexical feature bank file;
   identifying, by the computer, a set of lexical features in the text of a resource of the corpus according to the lexical feature bank file indicating one or more semantic features and one or more syntactic features, wherein the set of lexical features comprises at least one semantic feature in the bank file and at least one syntactic feature in the bank file, and wherein the computer receives the resource from a resource store;

storing, by the computer, into a database configured to store the corpus comprising the plurality of resources and metadata associated with each resource, metadata containing a first value associated with each of the lexical features in the set of lexical features according to the bank file, wherein the bank file indicates each value associated with each respective lexical feature;

determining, by the computer, a text difficulty score for the text using each of the first values associated with each of the features in the set of lexical features;

storing, by the computer, into the database storing the plurality of resources, metadata containing the text difficulty score associated with the text of each resource; and generating, by the computer, a portion of one or more lessons associated with a learner profile using the text of a resource selected from the database based upon metadata indicating one or more skill scores of the learner profile stored in a profile database and the metadata containing the text difficulty score of each of the resources of the corpus in the database;

wherein the computer receives one or more training resources containing text, wherein the one or more semantic and syntactic features of the text are labeled with metadata indicating the features and an associated first weighted value associated with each of the features; and wherein the lexical feature bank file includes each of the semantic and syntactic features labeled in the one or more training resources and each of the associated first weighted values.

9. The method according to claim 8, further comprising assigning, by the computer, a second value to each of the features in the set of lexical features, wherein the computer determines the text difficulty score for the text using each of the first values and each of the second values associated with each of the lexical features.

10. A system comprising:

a database comprising non-transitory machine-readable storage media configured to store a corpus comprising one or more resources, and metadata associated with each of the one or more resources in the corpus;

a learner database comprising non-transitory machine-readable storage media configured to store one or more learner profiles; and a computer comprising a processor and non-transitory machine-readable storage containing a text difficulty calculator module instructing the processor to execute the steps of:

identifying in text of a resource of the corpus a set of lexical features according to a lexical feature bank file, the set of lexical features including one or more semantic features and one or more syntactic features;

storing, into the database storing the resource of the corpus, metadata associated with each resource, the metadata containing a value associated with each of the identified semantic and syntactic features in the text according to the bank file, and metadata containing a statistical model associated with one or more resources of the corpus;

determining a text difficulty score associated with the resource using each of the values assigned to the identified semantic and syntactic features;

determining a text difficulty score of a new resource containing one or more lexical features, the text difficulty score of the new resource based upon the statistical model associated with the one or more resources of the corpus and the one or more lexical features of the new resource;

selecting from the database storing the plurality training resources, the new resource based upon one or more skill scores of a learner profile in the learner profile database and the text difficulty score in metadata of the new resource; and generating one or more portions of one or more language lessons associated with the learner profile using text of the new resource selected from the database;

wherein determining a text difficulty score associated with the resource comprises:

assigning a weight to each of the assigned values; and determining a weighted value for each of the identified syntactic and semantic features, wherein the text difficulty score is determined using the weighted values.

11. The system according to claim 10, further comprising outputting the text difficulty score to a computing device of a content curator.

12. The system according to claim 11, further comprising adjusting the text difficulty score according to an input received from the computing device of the content curator.

13. The system according to claim 10, further comprising:

grouping the resource with a set of one or more resources having a comparable text difficulty score; and categorizing resources into one or more sets of resources based on a difficulty category.

* * * * *